United States Patent [19]

Reagan et al.

[11] Patent Number: 5,288,823
[45] Date of Patent: Feb. 22, 1994

[54] CHROMIUM COMPOUNDS AND USES THEREOF

[75] Inventors: William K. Reagan, Stillwater, Minn.; Brian K. Conroy, Batavia, Ill.

[73] Assignee: Phillips Petroleum Company, Bartlesville, Okla.

[21] Appl. No.: 978,852

[22] Filed: Nov. 19, 1992

Related U.S. Application Data

[60] Division of Ser. No. 698,515, May 10, 1991, Pat. No. 5,198,563, which is a division of Ser. No. 454,554, Dec. 21, 1989, abandoned, which is a continuation-in-part of Ser. No. 392,688, Aug. 10, 1989, abandoned.

[51] Int. Cl.$^5$ ............................................. C08F 4/08
[52] U.S. Cl. ..................................... 526/124; 526/125; 526/161; 526/169
[58] Field of Search ............... 526/123, 124, 125, 161, 526/169

[56] References Cited

U.S. PATENT DOCUMENTS

| | | | |
|---|---|---|---|
| 3,231,550 | 1/1966 | Manyik et al. | 200/88.2 |
| 3,242,099 | 3/1966 | Manyik et al. | 252/429 |
| 3,300,458 | 1/1967 | Manyik et al. | 260/88.2 |
| 3,347,840 | 10/1967 | Manyik et al. | 260/94.9 |
| 4,115,319 | 9/1978 | Scatá et al. | 526/124 |
| 4,603,184 | 7/1986 | Sato et al. | 526/142 |
| 4,668,838 | 5/1987 | Briggs | 585/513 |
| 4,806,513 | 2/1989 | McDaniel et al. | 502/107 |
| 4,814,308 | 3/1989 | Konrad et al. | 502/107 |

OTHER PUBLICATIONS

*Grant & Hackh's Chemical Dictionary*, edited by Grant et al., McGraw-Hill Book Co., New York, 1987, p. 30.
Zeitschrift für Naturforschung, Pyrrodylchromium Compounds, 21 b, p. 1239 (D. Tille, 1966).
Z. Anorg. Alleg. Chem., Organometal Compounds of Nitrogen Systems, 384, pp. 136–146 (D. Tille, 1971).
J. Chem. Soc., Chem. Commun., Selective Trimenzation of Ethylene to Hex-1-ene, pp. 674–675 (J. Briggs, 1989).
ACS Preprints Symposia on Novel Preparation & Conversion of Light Olefins (Reagen, Aug. 1989).

*Primary Examiner*—Joseph L. Schofer
*Assistant Examiner*—R. H. Delmendo
*Attorney, Agent, or Firm*—Lynda S. Jolly

[57] ABSTRACT

Novel chromium-containing compounds, such as, for example, chromium pyrrolides, are prepared by forming a mixture of a chromium salt, a metal amide, and an electron pair donor solvent, such as, for example, an ether. These novel chromium-containing, or chromium pyrrolide, compounds can be used either unsupported or supported on an inorganic oxide support to trimerize and/or polymerize olefins.

27 Claims, 9 Drawing Sheets

CHROMIUM COMPOUNDS AND USES THEREOF

This application is a divisional application of Ser. No. 07/698,515, filed May 10, 1991 now U.S. Pat. No. 5,198,563, which is a division of Ser. No. 07/454,554, filed Dec. 21, 1989, abandoned, which is a continuation-in-part of application Ser. No. 07/392,688, filed Aug. 10, 1989, abandoned.

BACKGROUND OF THE INVENTION

This invention relates to chromium catalysts to trimerize and/or polymerize olefins. This invention also relates to a process to trimerize and/or polymerize olefins.

Supported chromium oxide catalysts have been a dominant factor in the production of olefin polymers, such as polyethylene of copolymers of ethylene and hexene. These catalysts can be used in a variety of polymerization processes. However, most known chromium compounds must be supported to be catalytically active. Furthermore, most supported chromium compounds are useful only for olefin polymerization. If an olefin copolymer is desired, the polymerization process becomes more complex in that two different monomers must be fed to the polymerization reactor.

Olefin trimerization catalysts are also known in the art, but usually lack selectivity to a desired product and also have a low product yield. However, olefin trimerization, if done efficiently, is a process to provide useful olefins, which in turn, can be further trimerized or, optionally, incorporated into a polymeriation process.

SUMMARY OF THE INVENTION

Therefore, it is an object of this invention to provide novel chromium compounds.

It is yet another object of this invention to provide a process to prepare at least one novel chromium compound.

It is a further object of this invention to provide an improved process to trimerize olefins.

It is yet another object of this invention to provide a process to polymerize olefins.

It is a further object of this invention to provide an improved olefin trimerization catalyst.

It is yet another object of this invention to provide an olefin polymerization catalyst.

Therefore, in accordance with this invention, novel chromium-containing compounds are prepared from a reaction mixture comprising a chromium salt, a metal amide, and any electron pair donor solvent, such as, for example, an ether.

In accordance with another embodiment of this invention this chromium-containing compound can be used, either supported or unsupported, to trimerize or polymerize olefins.

DETAILED DESCRIPTION OF THE INVENTION

The Chromium Compounds

Figure 1:
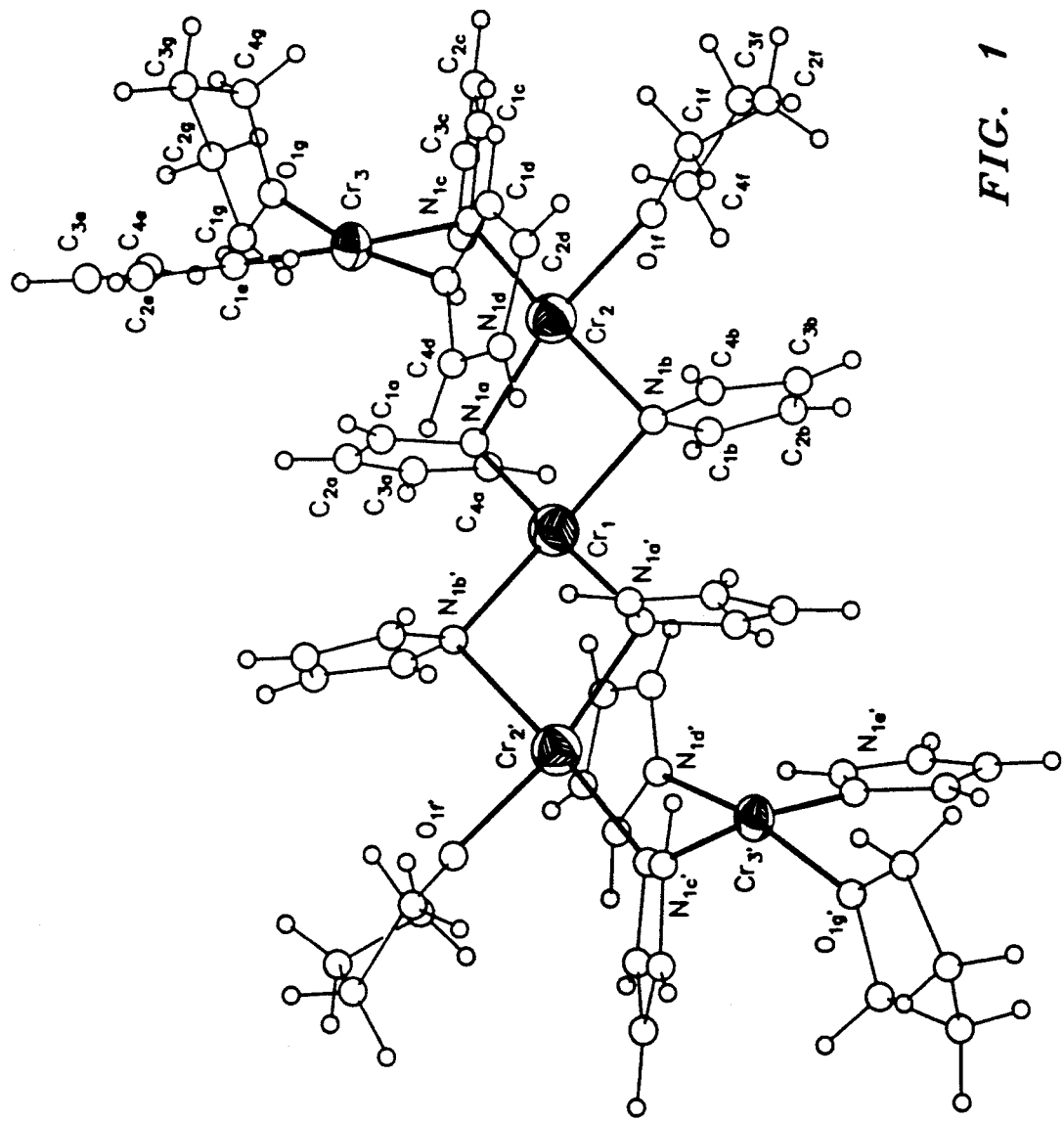
FIG. 1 is a computer generated ball and stick projection, with the exception of the chromium atoms which are represented as thermal ellipsoids, or a simplified structural representation or formula, of a molecule of Product I, $Cr_5(NC_4H_4)_{10}(OC_4H_8)_4$, as determined by single crystal x-ray crystallography.

The inventive chromium compounds, which can be used preferably for olefin trimerization and, optionally, olefin polymerization, can be produced by forming a reaction mixture comprising a chromium salt, a metal amide, and any electron pair donor solvent, such as, for example, an ether. As used in this disclosure, the inventive chromium compounds are referred to by a variety of interchangeable names, such as inventive or novel chromium compound(s), chromium complex(es), chromium pyrrole complex(es) and/or chromium pyrrolide.

The chromium salt can be one or more organic or inorganic chromium salts, wherein the chromium oxidation state is from 0 to 6. As used in this disclosure, chromium metal is included in this definition of a chromium salt. Generally, the chromium salt will have a formula of $CrX_n$, wherein X can be the same or different and can be any organic or inorganic radical, and n is an integer from 1 to 6. Exemplary organic radicals can have from about 1 to about 20 carbon atoms, and are selected from the group consisting of alkoxy, ester, ketone, and/or amido radicals. The organic radicals can be straight-chained or branched, cyclic or acyclic, aromatic or aliphatic, and can be made of mixed aliphatic, aromatic, and/or cycloaliphatic groups. Exemplary inorganic radicals include, but are not limited to halides, sulfates, and/or oxides.

Preferably, the chromium salt is a halide, such as, for example chromous bromide, chromic bromide, chromous iodide, chromic iodide, chromous fluoride, chromic fluoride, chromous chloride, chromic chloride, and mixtures thereof. Most preferably, the chromium salt is a chloride, such as, for example chromous chloride and/or chromic chloride, due to simple separation of the reaction by-products such as, for example, sodium chloride, as well as relatively low cost.

The metal amide can be any metal amide that will react with a chromium salt to form a chromium-amido complex. Broadly, the metal amide can be any heteroleptic or homoleptic metal complex or salt, wherein the amide radical can be any nitrogen-containing organic radical. The metal amide can be either affirmatively added to the reaction, or generated in-situ. Generally, the metal amide will have from about 1 to about 20 carbon atoms. Exemplary metal amides include, but are not limited to, primary and/or secondary amines, any alkali metal (Group IA, and including hydrogen, of the Periodic Table) amide and/or any alkaline earth metal (Group IIA of the Periodic Table) amide. The hydrocarbyl portion of the salt of the metal amide is selected from the group consisting of straight chain or branched, cyclic or acyclic, aromatic or aliphatic, and mixtures of two or more thereof. Preferably, the metal amide is selected from a Group IA, and including hydrogen, or Group IIA metal amide, due to ease of reaction with chromium halides.

Exemplary preferred metal amides include, but are not limited to, lithium dimethylamide, lithium diethylamide, lithium diisopropylamide, lithium dicyclohexylamide, sodium bis(trimethylsilyl)amide, sodium indolide, sodium pyrrolide, and mixtures of two or more thereof. Most preferably, the metal amide is a pyrrolide. As used in this disclosure, a pyrrolide is defined as a compound comprising a 5-membered, nitrogen-containing heterocycle, such as, for example, pyrrole, derivatives of pyrrole, and mixtures thereof. Exemplary pyrrolides are selected from the group consisting of hydrogen pyrrolide (pyrrole), lithium pyrrolide, sodium pyrrolide, potassium pyrrolide, cesium pyrrolide, and/or the salts of substituted pyrrolides, because of high reactivity and activity with the other reactants. Examples of salts of substituted pyrrolides include, but are not limited to sodium 2,5-dimethyl pyrrolide and/or 3,4-dimethyl pyrrolide. When the metal amide is a pyrrolide ligand, the resultant chromium compound is a chromium pyrrolide.

The electron pair donor solvent can be any electron pair donor solvent to affect a reaction between the chromium salt and the metal amide. While not wishing to be bound by theory, it is believed that the electron pair donor solvent can be a reaction solvent, as well as a possible reactant. Exemplary electron pair donor solvents include, but are not limited to, nitrogen-, oxygen-, phosphorous-, and/or sulfur-containing compounds and/or ethers.

Exemplary nitrogen-containing compounds include, but are not limited to nitriles, such as, for example, acetonitrile; amines, such as, for example, pyridine, and/or amides. Additional exemplary nitrogen-containing compounds include, but are not limited to, nitromethane, dimethylpyridine, dimethylformamide, N-methylformamide, aniline, nitrobenzene, tetramethyldiaminomethane, hexamethyldisilazane, and/or pyrrolidone.

Exemplary oxygen-containing compounds include, but are not limited to, acetone, ethyl acetate, methyl acetate, methanol, ethanol, ethyl methyl ketone, acetaldehyde, furan, and/or hexamethyldisiloxane.

Exemplary phosphorous-containing compounds include, but are not limited to, hexamethylphosphoramide, hexamethylphosphorous triamide, triethylphosphite, tributylphosphine oxide, and/or triethylphosphine.

Exemplary sulfur-containing compounds include, but are not limited to, carbon disulfide, dimethylsulfoxide, tetramethylene sulfone, triophene, and/or dimethylsulfide or mixtures thereof.

The ether in the reaction mixture can be one or more ether compounds to affect a reaction between the chromium salt and the metal amide. While not wishing to be bound by theory, it is believed that the ether can be a reaction solvent, as well as a possible reactant. The ether can be any aliphatic and/or aromatic compound containing an R-O-R functionality, wherein the R groups can be the same or different, but preferably is not hydrogen. Preferred ethers are aliphatic ethers, for safety reasons in that aromatic ethers are human toxins. Furthermore, the preferred ethers are those which facilitate a reaction between a chromium halide and a Group IA or Group IIA metal pyrrolide, and also can be easily removed from the reaction mixture. Exemplary compounds include, but are not limited to, tetrahydrofuran, dioxane, diethylether, dimethoxyethane (glyme), diglyme, triglyme, and mixtures of two or more dimethoxyethane (glyme), diglyme, triglyme, and mixtures of two or more thereof. Most preferably, the ether is selected from the group consisting of tetrahydrofuran, derivatives of tetrahydrofuran, dimethoxyethane, derivatives of dimethoxyethane, and mixtures thereof, for the reasons given above, as well as the reason that the preferred salt of an amine is soluble in these ethers.

The amount of each reactant used to prepare one or more of the novel chromium compounds can vary, based on the desired chromium compound product. Any amount of each reactant can be used to produce the novel chromium compounds, depending on the desired product. Different reaction stoichiometries can produce different chromium compounds. For example, the reaction of about one mole of chromium (II) with about two moles of sodium pyrrolide can produce different products than reacting about one mole of chromium (II) with an excess of sodium pyrrolide. Furthermore, as stated earlier, selection of different, although similar reactants, can produce different products. For example, using either tetrahydrofuran or dimethoxyethane can result in a different reaction product.

The three reactants can be combined in any manner under conditions suitable to form a solution comprising one or more of the inventive chromium compounds. The reaction preferably occurs in the absence of oxygen and therefore under an inert, such as, for example, nitrogen and/or argon. The reaction pressure can be any pressure sufficient to maintain the reactants in a liquid state. Generally, pressure within the range of from about atmospheric pressure to about three atmospheres are acceptable. For ease of operation atmospheric pressure is generally employed.

The reaction temperature can be any temperature which maintains the ether in a liquid form. In order to effectuate a more efficient reaction, temperatures near the boiling point of the ether are preferred. Most preferably, the reaction temperature is at the boiling point of the ether and the reaction mixture is refluxed for a period of time.

The reaction time can be any amount of time necessary for the reaction to occur. Depending on the reactants, as well as the reaction temperature and pressure, reaction time can vary from about 1 minute to about 1 week. Usually, reaction time ranges from about 3 hours to about 5 days. Under optimum conditions, the reaction time can be within the range of from about 3 to about 48 hours.

After the reaction is complete, a solid reaction product can be recovered by any method known in the art. Preferably, though not required, upon completion of the reaction, the reaction mixture first is filtered to remove any reaction insoluble by-products such as, for example, salts, like sodium chloride, prior to any other treatment. Although removal of any reaction by-products is not necessary, such removal preferably is done in order to expedite later purification of the chromium product. After filtering, one exemplary method to recover a solid reaction product is to remove the excess ether from the reaction mixture. The excess electron pair donor solvent, such as, for example an ether, can be removed according to any method known in the art. Exemplary electron pair donor solvent, such as, for example an ether, removal methods include, but are not limited to, slow evaporation, under vacuum and/or a nitrogen purge.

Other electron pair donor solvent, such as, for example an ether, removal procedures can be used either alone or in combination. For example, the reaction mixture can be filtered and then vacuum dried. Preferably, the reaction mixture is heated slowly and maintained at temperature within the range of about 10° C. to about 300° C., preferably about 25° C. to about 200° C., under a vacuum, for safety, to remove the excess electron pair donor solvent, such as, for example an ether. The resultant solid reaction product is one or more of the inventive chromium compounds.

Alternatively, the reaction mixture can be filtered to remove any solid reaction by-product solids and the filtered reaction mixture can be contacted with a non-polar organic solvent. Addition of a non-polar organic solvent causes one or more of the inventive chromium compounds to form a solid precipitate. Exemplary non-polar organic solvent include, but are not limited to, pentane, hexane, cyclohexane, heptane, and mixtures thereof. Most preferably pentane is added to the filtered reaction mixture because of the availability and ease of use.

The precipitated inventive chromium compounds can be recovered by any method known in the art. The simplest procedure to recover the inventive precipitated chromium compounds is by filtration.

The reaction mixture and the resultant solid reaction products, as stated earlier, are kept in an oxygen-free atmosphere at all times. Preferably, due to availability and ease of use, an inert atmosphere such as, for example, nitrogen, is the ambient.

Numerous chromium compounds can be prepared in accordance to the invention, by varying the reactants and/or the quantity of each reactant employed. The recovered, novel chromium compound or compounds can be used for olefin trimerization and/or polymerization without further purification.

Optionally, the chromium compound can be purified in accordance with any method known in the art. For example, one of the simplest purification procedures is to wash the recovered solid with a non-polar organic solvent such as, for example, toluene. Preferably, a non-polar aliphatic organic solvent is used for best results. Exemplary wash solvents include, but are not limited to, pentane, hexane, cyclohexane, heptane, and mixtures thereof. Most preferably, pentane is the wash solvent.

The inventive chromium compounds can be used as a supported and/or unsupported catalyst for olefin trimerization and/or polymerization. A supported chromium catalyst can be prepared according to any method known in the art. Any support useful to support chromium catalyst can be used. Exemplary catalyst supports include, but are not limited to, inorganic oxides, either alone or in combination, phosphated inorganic oxides, and mixtures thereof. Particularly preferred are supports selected from the group consisting of silica, silica-alumina, alumina, fluorided alumina, silated alumina, thoria, aluminophosphate, aluminum phosphate, phosphated silica, phosphated alumina, silica-titania, coprecipitated silica/titania, and mixtures, thereof, fluorided/silated alumina, being presently preferred, as well as any one or more of these supports which can contain chromium. The presently most preferred catalyst support is because of the greatest trimerization activity, is aluminophosphate, as disclosed in U.S. Pat. No. 4,364,855 (1982), herein incorporated by reference.

The supported chromium catalyst system can be prepared according to any method known in the art. For example, the reaction mixture, which preferably has been filtered to remove any particulate reaction by-products and contains one or more of the novel chromium pyrrolide compounds, is combined and thoroughly contacted with a catalyst support. Excess electron pair donor solvent, such as, for example an ether, does not have to be removed prior to contacting the catalyst support. However, a solid chromium pyrrolide compound can be re-dissolved in an electron pair donor solvent, such as, for example an ether, if desired. The chromium pyrrolide/ether solution is usually a blue or blue/green color, although other colors can be observed.

The catalyst support usually is insoluble in the ether/chromium pyrrolide complex solution. Any excess of the chromium pyrrolide in relation to the catalyst support is sufficient. However, usually, at least about 5 grams of chromium pyrrolide compound per gram of catalyst support is sufficient. Preferably about 0.001 to about 1 grams of chromium pyrrolide compound per gram of support, and most preferably about 0.01 to about 0.5 grams of chromium pyrrolide compound per gram of support is used for best support loading and most efficient use of the reagents. This mixture can be contacted and mixed at any time, temperature, and pressure to thoroughly contact the chromium pyrrolide compound and support. For ease of use, ambient temperatures and pressures are preferred. Mixing times can be up to about 24 hours, preferably about 5 seconds to about 10 hours, and most preferably about 5 seconds to about 8 hours. Longer times usually provide no additional benefit and shorter times can be insufficient for thorough contacting.

After the support is added and thoroughly combined with the chromium pyrrolide it is collected by filtration, vacuum dried, then an activating compound, usually as a solution of one or more Lewis acids and/or metal alkyls, preferably in a hydrocarbon solvent, is added to the support/chromium pyrrolide mixture. As used in this disclosure, a Lewis acid is defined as any compound that is an electron acceptor. Preferably, the activating compound is a compound that can be considered both a Lewis acid and a metal alkyl. Preferred activating compounds which are both a metal alkyl and a Lewis acid include, but are not limited to, alkylaluminum compounds, and mixtures thereof. The most preferred alkylaluminum compound is triethylaluminum, for best results in catalyst activity.

The hydrocarbon solvent can be any hydrocarbon that will dissolve the Lewis acid. Preferred hydrocarbons include, but are not limited to, aromatic compounds having from about 6 to about 50 carbon atoms per molecule. Most preferably, the hydrocarbon solvent is toluene, for ease of removal and minimal interference with the resultant catalyst.

Any amount of activating compounds, such as a metal alkyl and/or a Lewis acid is sufficient to activate and/or react with the chromium pyrrolide catalyst. Usually about 200 grams of Lewis acid per gram of chromium can be used. Preferably, about 1 to about 100 grams of activating compound, such as a metal alkyl and/or a Lewis acid per gram of chromium pyrrolide, and most preferably about 5 to about 30 grams of activating compound, such as a metal alkyl and/or a Lewis acid per gram of chromium pyrrolide are used, for best catalyst activity. However, the amount of Lewis acid employed can vary with the catalyst support used. For example, if the support is silica and/or alumina, too much activating compound, such as a metal alkyl and/or a Lewis acid can decrease catalyst activity. However, a similar amount of activating compound, such as a metal alkyl and/or a Lewis acid used with an aluminophosphate support does not always significantly decrease catalyst activity.

As disclosed earlier, the mixture of chromium pyrrolide, catalyst support, and activating compound, such as a metal alkyl and/or a Lewis acid are mixed and/or contacted under a dry, inert atmosphere at all times. Any pressure can be used during the contacting; for ease of use, atmospheric pressure is preferred. Any temperature can be used during the contacting; for ease of use, room temperature, or ambient temperature, is preferred. Some care should be taken during the mixing, so as not to destroy the physical integrity of the chromium pyrrolide, catalyst support, and resultant supported catalyst. The three-component mixture can be contacted for any amount of time sufficient to prepare and activate a chromium catalyst. Usually times in the the range of about one minute to about one week are sufficient. Preferably, times in the range of about 30 minutes to about 24 hours are used, and most preferably times in the range of about one hour to about 12 hours are used. Too short of mixing times can result in incomplete contacting and too long of mixing times will not provide any additional catalytic benefit.

An alternative, and presently preferred, method to produce a supported catalyst is to combine one or more solid, inventive chromium pyrrolide compounds with a hydrocarbon solvent, a disclosed earlier, such as, for example, toluene, and an activating compound, such as a metal alkyl and/or a Lewis acid, as disclosed earlier, such as, for example, triethylaluminum. This mixture can be stirred for any time sufficient to dissolve the chromium pyrrolide compound, at any pressure or temperature. Usually, times of about one minute to about one week, preferably about one hour to about 24 hours, and most preferably within the range of about three hours to about 12 hours are used. For ease of operation, ambient temperatures and pressures are used. Usually, a brown solution will result.

After the solution is sufficiently mixed, a support is added to the solution and stirred to thoroughly contact the solution and support. The quantity of support is any amount sufficient to support the chromium pyrrolide compound. Generally, the amount of support necessary is the same as that disclosed in the previous ememplary process. Any suitable pressure and temperature can be used, although ambient temperature and pressure are preferred for ease of use. Usually, the mixing and/or contacting time is within the range of about 30 minutes to about one week, preferably from about 3 hours to about 48 hours. Most preferably, the mixing and/or contacting time is within the range of about 5 hours to about 24 hours, to maximize efficiency and result in a thoroughly contacted support.

The solution then can be filtered to recover a solid catalytic product. The catalytic product, as with the reactants and reactions, is preferably kept under an inert atmosphere to maintain chemical stability.

If the chromium compound, such as, for example, a chromium pyrrolide, is recovered and is to be used as an unsupported trimerization and/or polymerization catalyst, olefins can be trimerized or polymerized in a presence of one or more of the inventive homogeneous chromium compounds, a saturated hydrocarbon as a diluent, and Lewis acid. Optionally, hydrogen can be added to the reactor to accelerate the reaction.

Reactants

Reactants applicable for use in polymerization with the catalyst and processes of this invention are olefinic compounds which can polymerize, i.e., react the same or with other olefinic compounds. Catalyst of the invention can be used to polymerize at least one linear or branched mono-1-olefin having about 2 to about 8 carbon atoms. Exemplary compounds include, but are not limited to, ethylene, propylene, 1-butene, 1-pentene, 1-hexene, 1-octene, and mixtures thereof.

Reactants applicable for use in the trimerization process, i.e., the combination of any three olefins, of this invention are olefinic compounds which can a) self-react, i.e., trimerize, to give useful products such as, for example, the self reaction of ethylene can give one hexene; and/or b) olefinic compounds which can react with other olefinic compounds, i.e., co-trimerize, to give useful products such as, for example, co-trimerization of ethylene plus hexene can give one decene and/or 1-tetradecene, co-trimerization of ethylene and 1-butene gives one octene, or 1-decene and ethylene can give 1-tetradecene and/or 1-docosene. As used herein, the term "trimerization" is intended to include "co-trimerization" as defined above.

Suitable trimerizable olefinic compounds are those compounds having from about 2 to about 30 carbon atoms per molecule and having at least one olefinic double bond. Exemplary compounds include, but are not limited to acyclic and cyclic olefins such as, for example, ethylene, propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes, and mixtures of any two or more thereof. If branched and/or cyclic olefins are used as reactants, while not wishing to be bound by theory, it is believed that steric hindrance could hinder the trimerization process. Therefore, the branched and/or cyclic portion(s) of the olefin should be distant from the carbon-carbon double bond.

The reaction products, i.e., trimers and/or polymers, can be prepared from the catalyst systems of this invention by solution reactions, slurry reactions, and/or gas phased reaction techniques using conventional equipment and contacting processes. Contacting of the monomer or monomers with the catalyst system can be effected by any manner known in the art of solid catalyst. One convenient method is to suspend the catalyst system in an organic medium and to agitate the mixture to maintain the catalyst system in suspension throughout the trimerization and/or polymerization process. Other known contacting methods such as fluidized bed, gravitating bed, and fixed bed can also be employed. Optionally, hydrogen can be added to the reactor to accelerate the reaction.

The catalyst systems of this invention are particularly suitable for use in slurry trimerization and/or polymerizations. The slurry process is generally carried out in an inert diluent (medium), such as a paraffin, cycloparaffin, or aromatic hydrocarbon. One exemplary reactor diluent is isobutane. When the reactant is predominately ethylene, a temperature in the range of about 60° to about 110° C. is employed.

Products

The olefinic and/or polymeric products of this invention have established utility in a wide variety of applications such as, for example, as monomers for use in the preparation of homopolymers, copolymers, and/or terpolymers. The polymeric products of this invention have established utility in a wide variety of applications such as for example, polyethylene.

The further understanding of the present invention and its advantages will be provided by reference to the following examples.

EXAMPLES

Preparation of Chromium-Containing Compounds

Manipulations of all reactants were carried out either in a drybox employing nitrogen, or in airless glassware employing vacuum or nitrogen. Tetrahydrofuran (THF), toluene, benzene, diethylbenzene (Aldrich, 97% mixture of 1,2-, 1,3-, 1,4-isomers) and pentane were purified by distillation over sodiumbenzophenone ketyl under nitrogen, then degassed via a nitrogen purge. Dimethoxyethane (DME) (Aldrich, anhydrous) was degassed via nitrogen purge and used without further purification. Pyrrole (Aldrich, 98%) was vacuum distilled over sodium, then degassed via nitrogen purge. 2,5-Dimethylpyrrole was dried with calcium sulfate and vacuum distilled. Sodium 2,5-dimethylpyrrolide ($NaC_6H_8N$) was prepared by reacting 2,5-dimethylpyrrole with an excess of sodium (40% by weight dispersion in mineral spirits) in refluxing tetrahydrofuran under nitrogen. Sodium pyrrolide was prepared by reacting pyrrole with an equivalent molar amount (1:1) of NaH (Aldrich, 60% by weight in mineral oil) or sodium (40% dispersion by weight in mineral spirits) in dimethoxyethane or tetrahydrofuran (THF) at ambient temperature under nitrogen. Triethylaluminum (TEA) (Aldrich 1.0M, hexanes and 1.9M toluene) was used as received. Ketjen Grade B alumina ($Al_2O_3$) and Davison 952 silica ($SiO_2$) were the commercial materials used as supports for catalyst preparations. Fluorided-alumina ($F/Al_2O_3$, 15 wt % F) was prepared by the addition of a solution of $NH_4HF_2$ in methanol to Ketjen Grade B alumina. Phosphated silica ($P/SiO_2$, P/Si molar ratio=0.1) was prepared by the addition of a 10% $H_3PO_4$/methanol solution to Davison 952 silica. The aluminophosphate ($AlPO_4$) used in the following experiments was made as described in McDaniel et al, U.S. Pat. No. 4,364,855 (1982). The supports were activated by placing up to 25 g into a fritted quartz tube, fluidizing with air and calcining at 700° C., except for $P/SiO_2$ at 350° C., for 3 hours. The air stream was switched to nitrogen until the support cooled to ambient temperature.

Chromium pyrrolide complexes were typically prepared from anhydrous chromium (II or III) chloride and sodium pyrrolide as follows:

A typical synthetic procedure useful to prepare chromium pyrrolide complexes was that of reacting the chromium chlorides with sodium pyrrolide ($NaC_4H_4N$, also referred to as NaPy) in refluxing tetrahydrofuran (THF). A molar reactant stoichiometry of $1CrCl_2$ and 2NaPy resulted in the isolation of a polymeric material, Product II, as the major product and a pentanuclear complex, Product I, ($Cr_5(NC_4H_4)_{10}(OC_4H_8)_4$), as the minor product, see Equation 1. Using molar excess of NaPy resulted in the isolation of the dianionic square planar complex $\{Cr(NC_4H_4)_4\}\{Na\}_2.20OC_4H_8$, Product III, and the octahedral complex $\{Cr(C_4H_4N)_5(OC_4H_4)\}\{Na\}_2 4OC_4H_8$, Product IV, see Equation 2. Each of the products was isolated through precipitation, Product II, or crystallization, Products I, III, IV, from THF solutions by the addition of pentane.

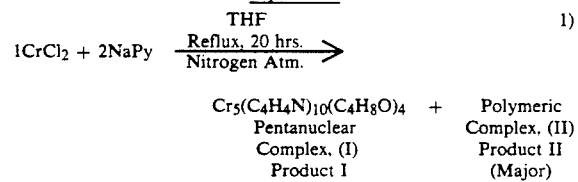

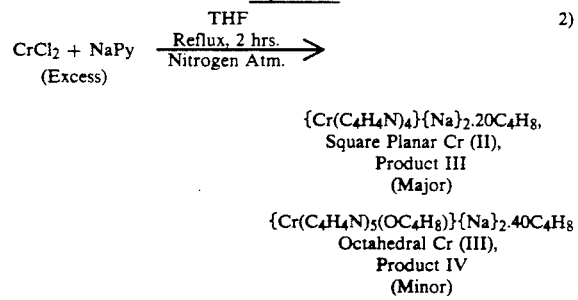

EXAMPLE I

To prepare the pentanuclear complex, Product I, ($Cr_5(NC_4H_4)_{10}(OC_4H_8)_4$), and the polymeric material, Product II, chromous chloride (2.0 g/16.27 mmole) was combined with sodium pyrrolide (33.68 mmole) in tetrahydrofuran and refluxed 20 hours. The reaction mixture was filtered (medium porosity frit) and the filtrate was used for fractional crystallization of both ($Cr_5(NC_4H_4)_{10}(OC_4H_8)_4$), Product I, and the polymeric material, Product II, through the addition of pentane. The polymeric material crystallized as a blue solid followed by ($Cr_5(NC_4H_4)_{10}(OC_4H_8)_4$) as opaque dark blue/purple crystals.

Figure 2:
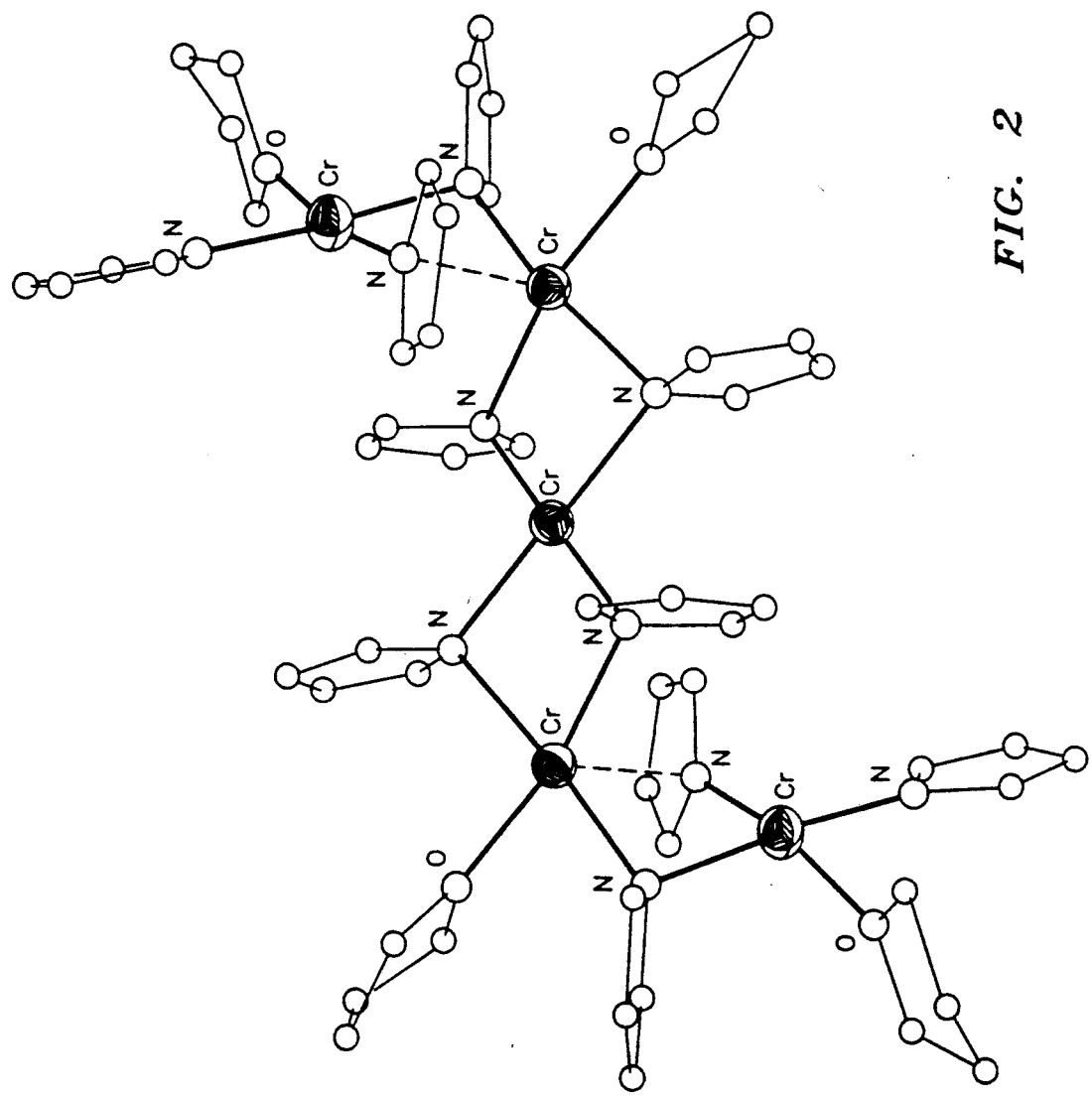
FIG. 2 is a further simplified ball and stick projection, with the exception of the chromium atoms which are represented as thermal ellipsoids, or a structural representation, of the same molecule shown in FIG. 1.

Analysis calculated for $C_{56}H_{72}N_{10}Cr_5$, Product I: C, 55.62; H, 6.00; N, 11.58%, by weight. Found: C, 55.46; H, 6.32; N, 11.15%, by weight. Analysis found for Product II: Cr, 11.5; C, 59.75; H, 7.61; N, 9.17%, by weight, but variable upon precipitation conditions. An x-ray crystal structure of Product I showed a pentanuclear complex incorporating bridging amido-pyrrolyl, terminal amido-pyrrolyl, and tetrahydrofuran ligands (FIGS. 1 and 2).

EXAMPLE II

To prepare $\{Cr(NC_4H_4)_4\}\{Na\}_2 \cdot 2OC_4H_8$, Product III, and $\{Cr(C_4H_4N)_5(OC_4H_8)\}\{Na\}_2 \cdot 4OC_4H_8$, Product IV, chromous chloride (3.0 g/24.4 mmole) was combined with sodium pyrrolide (100.9 mmole) in tetrahydrofuran and refluxed 2 hours, see Equation 2. The reaction mixture was filtered (medium porosity frit) and the filtrate was used for fractional crystallization of both $\{Cr(NC_4H_4)_4\}\{Na\}_2 \cdot 2OC_4H_8$, Product III, and $\{Cr(C_4H_4N)_5(OC_4H_8)\}\{Na\}_2 \cdot 4OC_4H_8$, Product IV, through the addition of pentane. Product III crystallized as translucent orange/red crystals followed by Product IV as translucent purple crystals. While not wishing to be bound by theory, the formation of Product IV is believed to result from the presence of chromic chloride in the chromous chloride reagent (Alfa, chromium (II) chloride, anhydrous, contains 5–10% by weight $CrCl_3$) used in the preparation.

Figure 4:
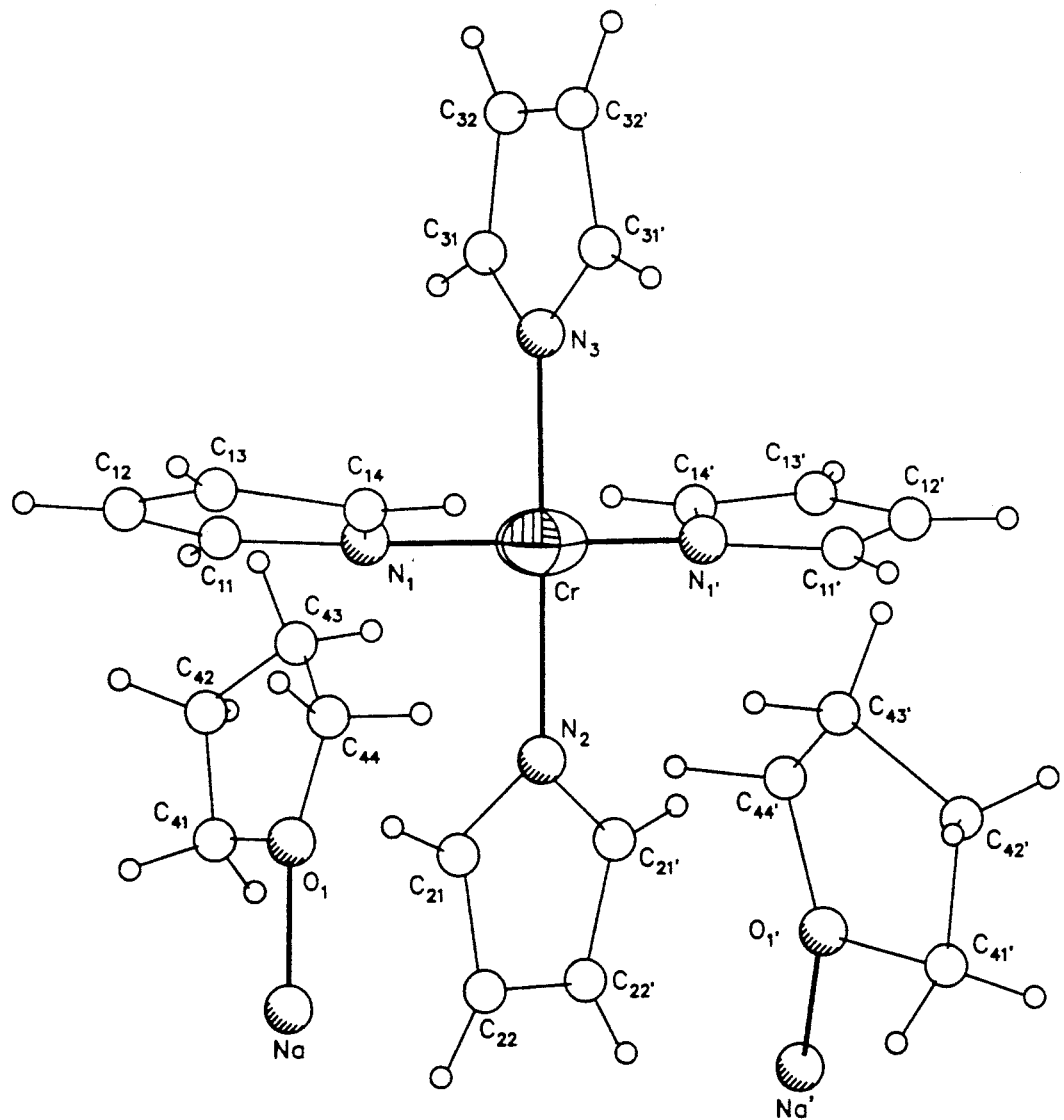
FIG. 4 is a further simplified ball and stick projection, with the exception of the chromium atoms which are represented as thermal ellipsoids, or a structural representation, of the same molecule shown in FIG. 3, however, the entire crystal structure or lattice, with the formula $Cr(NC_4H_4)_4Na_2.20C_4H_8$ is shown.
Figure 5:
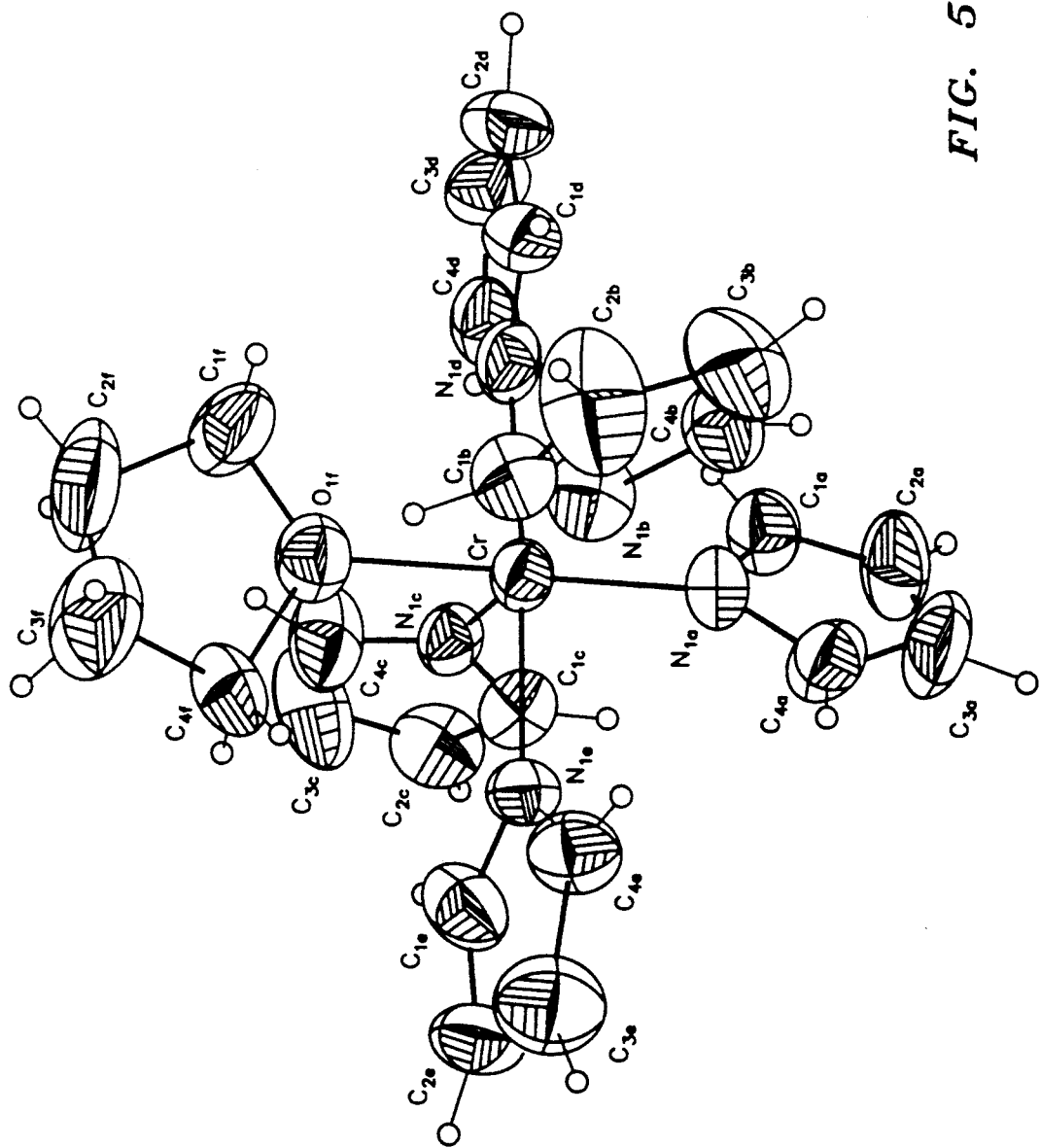
FIG. 5 is a computer generated ORTEP drawing of the structure, or a simplified structural representation or formula, of a molecule of Product IV, $[Cr(NC_4H_4)_5(OC_4H_8)]^{-2}$, as determined by single crystal x-ray crystallography.
Figure 6:
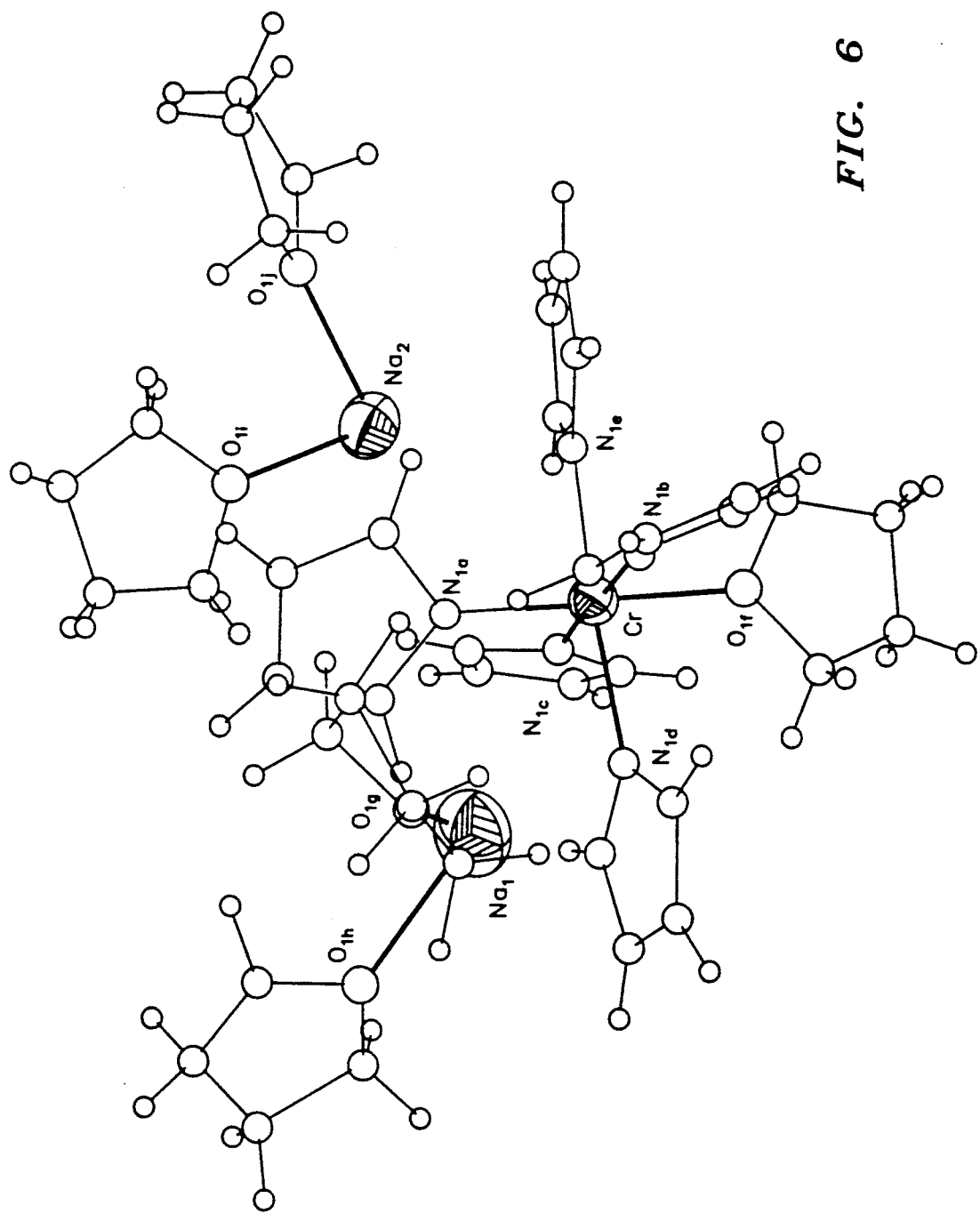
FIG. 6 is a further simplified ball and stick projection, with the exception of the chromium atoms which are represented as thermal ellipsoids, or a structural representation, of the same molecule shown in FIG. 5, however the entire crystal structure or lattice, with the formula $[Cr(NC_4H_4)_5(OC_4H_8)][Na]_2.4(OC_4H_8)$, is shown.

Analysis calculated for $C_{24}H_{32}N_4O_2CrNa_2$, Product III: C, 56.94; H, 6.32; N, 11.07% by weight. Found: C, 57.04; H, 6.30; N, 10.92%, by weight. Analysis calculated for $C_{40}H_{60}N_5O_5CrNa_2$, Product IV: C, 60.90; H, 7.67; N, 8.88% by weight. Found: C, 60.81; H, 7.74; N, 9.44%, by weight. An x-ray crystal structure of Product III showed a square planar complex incorporating terminal amido-pyrrolyl ligands (FIG. 4). An x-ray crystal structure of Product IV showed an octahedral complex incorporating terminal amido-pyrrolyl and a tetrahydrofuran ligand (FIGS. 5 and 6).

EXAMPLE III

The reaction product obtained from sodium pyrrolide and $CrCl_3$ was the most preferred in the preparation of an active catalyst. Pyrrole (7.0 ml/100.9 mmole) was mixed with NaH (4.2 g of 60%, about 105 mmole) in dimethoxyethane at ambient temperature until bubbling ceased. Chromic chloride (5.33 g/33.7 mmole) was added to the solution at ambient temperature. The reaction mixture was refluxed under nitrogen for five hours, see Equation 3. This resulted in a dark green solution. The solution was filtered (medium porosity frit) and stripped of solvent under vacuum and pumped dry under vacuum for 12 hours. The resultant chromium pyrrolide complex was a green solid, Product V. It was used in the preparation of an active catalyst without further purification.

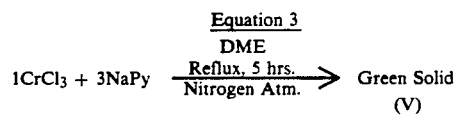

Equation 3

$1CrCl_3 + 3NaPy \xrightarrow[\text{Nitrogen Atm.}]{\text{DME}} $ Green Solid (V)   3)

EXAMPLE IV

All single crystal x-ray structure analyses were performed by Crystalytics Company, Lincoln, Nebr. Examples IV, V, VI, and IX contain the resultant analytical and subsequently computer-generated data.

A single crystal x-ray structure was obtained for $[Cr_5(NC_4H_4)_{10}(OC_4H_8)_4]$, Product I, and shown in FIGS. 1 and 2. The description of the single-crystal sample and amounting used for the collection are as follows:

Color: Dark blue
Shape: Rectangular parallelepiped
Dimensions: 0.20×0.48×0.80 mm
Crystal Mount: Crystal was sealed inside a thin-walled glass capillary with epoxy under $N_2$.
Crystal Orientation: Crystal was oriented with its longest edge nearly parallel to the phi axis of the diffractometer.
Width at half-height from $\omega$ Scans: 0.38°
The space group and cell data are as follows:
Crystal System: Triclinic
Space Group and Number:[2] $P1-C_i^1$ (No. 2)
Number of Computer-Centered Reflections Used in the Least-Squares
Refinement of the Cell Dimensions: 15 20°>25°, °C.=20°±1°
Lattice Constants with esd's:

| | | |
|---|---|---|
| a = 10.803(2)Å | α = 85.59(2)° | V = 1407.9(6)Å$^3$ |
| b = 9.825(2)Å | β = 96.23(2)° | Z = 1 |
| c = 14.212(4)Å | γ = 109.99(2)° | λ = 0.71073Å |

Molecular Weight: 1209.24 amu
Calculated Density: 1.427 g/cm$^{-1}$
Linear Absorption Coefficient:[3a] 0.96 mm$^{-1}$
Tables I–V list the resultant parameters used to generate the molecular structures shown in FIGS. 1 and 2.

TABLE I

Atomic Coordinates for Nonhydrogen Atoms in Crystalline $[Cr_5(NC_4H_4)_{10}(OC_4H_8)_4]^a$

| Atom Type[b] | Fractional Coordinates | | | Equivalent Isotropic Thermal Parameter, B, Å$^2$ × 10$^c$ |
|---|---|---|---|---|
| | 10$^4$x | 10$^4$y | 10$^4$z | |
| Cr$_1$ | 0$^d$ | 0$^d$ | 0$^d$ | 25(1) |
| Cr$_2$ | 636(1) | 2281(1) | 1500(1) | 24(1) |
| Cr$_3$ | −1179(1) | 841(1) | 3122(1) | 28(1) |
| N$_{1a}$ | −1155(3) | 935(3) | 715(2) | 25(1) |
| C$_{1a}$ | −2195(4) | 64(4) | 1231(3) | 31(1) |
| C$_{2a}$ | −3313(4) | 390(5) | 965(3) | 41(1) |
| C$_{3a}$ | −3014(4) | 1486(5) | 257(3) | 43(1) |
| C$_{4a}$ | −1728(4) | 1791(4) | 116(3) | 34(1) |
| N$_{1b}$ | 1566(3) | 1902(3) | 331(2) | 29(1) |
| C$_{1b}$ | 1753(4) | 3095(4) | −308(3) | 36(1) |
| C$_{2b}$ | 3035(5) | 3751(5) | −432(3) | 51(2) |
| C$_{3b}$ | 3736(4) | 2986(5) | 131(3) | 51(2) |
| C$_{4b}$ | 2823(4) | 1865(4) | 587(3) | 38(1) |
| N$_{1c}$ | −320(3) | 2997(3) | 2480(2) | 27(1) |
| C$_{1c}$ | 375(4) | 3732(4) | 3273(3) | 34(1) |
| C$_{2c}$ | 29(5) | 4919(4) | 3383(3) | 43(1) |
| C$_{3c}$ | −908(5) | 4967(4) | 2631(3) | 42(1) |
| C$_{4c}$ | −1105(4) | 3809(4) | 2101(3) | 32(1) |
| N$_{1d}$ | 443(3) | 350(3) | 2743(2) | 28(1) |
| C$_{1d}$ | 1600(4) | 715(4) | 3289(3) | 36(1) |
| C$_{2d}$ | 2321(4) | −133(5) | 3102(3) | 46(2) |
| C$_{3d}$ | 1567(5) | −1070(5) | 2403(3) | 46(2) |
| C$_{4d}$ | 422(4) | −763(4) | 2203(3) | 36(1) |
| N$_{1e}$ | −1972(3) | −1122(3) | 3801(2) | 35(1) |
| C$_{1e}$ | −1344(5) | −2107(4) | 4069(3) | 41(1) |
| C$_{2e}$ | −2189(5) | −3307(4) | 4503(3) | 44(1) |
| C$_{3e}$ | −3361(5) | −3061(4) | 4531(3) | 47(1) |
| C$_{4e}$ | −3206(5) | −1731(4) | 4097(3) | 47(1) |
| O$_{1f}$ | 2351(3) | 3985(3) | 1883(2) | 32(1) |
| C$_{1f}$ | 3536(4) | 4018(4) | 2483(3) | 43(1) |
| C$_{2f}$ | 4470(6) | 5479(6) | 2336(5) | 76(2) |
| C$_{3f}$ | 3642(5) | 6408(5) | 2147(4) | 62(2) |

TABLE I-continued

Atomic Coordinates for Nonhydrogen Atoms in Crystalline $[Cr_5(NC_4H_4)_{10}(OC_4H_8)_4]^a$

| Atom Type[b] | Fractional Coordinates $10^4x$ | $10^4y$ | $10^4z$ | Equivalent Isotropic Thermal Parameter, B, Å$^2$ × 10[c] |
|---|---|---|---|---|
| C$_{4f}$ | 2396(4) | 5463(4) | 1635(3) | 40(1) |
| O$_{1g}$ | −2551(3) | 1543(3) | 3659(2) | 35(1) |
| C$_{1g}$ | −3763(4) | 1733(5) | 3232(3) | 44(1) |
| C$_{2g}$ | −4097(5) | 2625(6) | 3907(4) | 57(2) |
| C$_{3g}$ | −3524(5) | 2241(6) | 4845(3) | 57(2) |
| C$_{4g}$ | −2319(5) | 1977(6) | 4633(3) | 50(2) |

[a] The numbers in parentheses are the estimated standard deviations in the last significant digit.
[b] Atoms are labeled in agreement with FIG. 1.
[c] This is one-third of the trace of the orthogonalized B$_{ij}$ tensor.
[d] This is a symmetry-required value and is therefore listed without an estimated standard deviation.

TABLE II

Anisotropic Thermal Parameters for Nonhydrogen Atoms in Crystalline $[Cr_5(NC_4H_4)_{10}(OC_4H_8)_4]^{a,b}$

| Atom Type[c] | Anisotropic Thermal Parameter (Å$^4$ × 10) | | | | | |
|---|---|---|---|---|---|---|
| | B$_{11}$ | B$_{22}$ | B$_{33}$ | B$_{12}$ | B$_{13}$ | B$_{23}$ |
| Cr$_1$ | 20(1) | 23(1) | 32(1) | 5(1) | 5(1) | −4(1) |
| Cr$_2$ | 23(1) | 22(1) | 27(1) | 7(1) | 3(1) | −2(1) |
| Cr$_3$ | 27(1) | 26(1) | 34(1) | 11(1) | 8(1) | 1(1) |
| N$_{1a}$ | 21(1) | 27(1) | 29(1) | 8(1) | 1(1) | −2(1) |
| C$_{1a}$ | 28(2) | 31(2) | 30(2) | 4(1) | 8(1) | −4(1) |
| C$_{2a}$ | 23(2) | 49(2) | 49(2) | 8(2) | 5(2) | −16(2) |
| C$_{3a}$ | 31(2) | 51(2) | 52(2) | 22(2) | −7(2) | −11(2) |
| C$_{4a}$ | 36(2) | 32(2) | 34(2) | 15(1) | −2(1) | −3(1) |
| N$_{1b}$ | 24(1) | 25(1) | 35(1) | 3(1) | 5(1) | −4(1) |
| C$_{1b}$ | 40(2) | 31(2) | 33(2) | 2(1) | 11(1) | −1(1) |
| C$_{2b}$ | 46(2) | 42(2) | 54(2) | −7(2) | 24(2) | −5(2) |
| C$_{3b}$ | 25(2) | 50(2) | 71(3) | −3(2) | 15(2) | −27(2) |
| C$_{4b}$ | 29(2) | 38(2) | 48(2) | 10(1) | 0(2) | −15(2) |
| N$_{1c}$ | 28(1) | 25(1) | 30(1) | 11(1) | 3(1) | −2(1) |
| C$_{1c}$ | 36(2) | 35(2) | 31(2) | 10(1) | 4(1) | −3(1) |
| C$_{2c}$ | 52(2) | 34(2) | 43(2) | 13(2) | 6(2) | −13(1) |
| C$_{3c}$ | 51(2) | 31(2) | 50(2) | 22(2) | 5(2) | −5(2) |
| C$_{4c}$ | 35(2) | 34(2) | 31(2) | 16(1) | 4(1) | 1(1) |
| N$_{1d}$ | 32(1) | 23(1) | 31(1) | 12(1) | 6(1) | 3(1) |
| C$_{1d}$ | 33(2) | 32(2) | 42(2) | 9(1) | 6(2) | −0(1) |
| C$_{2d}$ | 36(2) | 50(2) | 59(2) | 24(2) | 6(2) | 11(2) |
| C$_{3d}$ | 61(3) | 44(2) | 47(2) | 36(2) | 11(2) | 3(2) |
| C$_{4d}$ | 49(2) | 35(2) | 31(2) | 23(2) | 4(2) | 1(1) |
| N$_{1e}$ | 36(2) | 30(1) | 42(2) | 13(1) | 14(1) | 4(1) |
| C$_{1e}$ | 46(2) | 36(2) | 46(2) | 20(2) | 10(2) | 6(2) |
| C$_{2e}$ | 64(3) | 30(2) | 37(2) | 15(2) | 7(2) | 4(1) |
| C$_{3e}$ | 55(3) | 31(2) | 46(2) | −1(2) | 18(2) | −0(2) |
| C$_{4e}$ | 39(2) | 38(2) | 62(2) | 9(2) | 17(2) | 4(2) |
| O$_{1f}$ | 29(1) | 25(2) | 40(1) | 6(1) | −1(1) | −2(1) |
| C$_{1f}$ | 34(2) | 44(2) | 45(2) | 9(2) | −8(2) | −6(2) |
| C$_{2f}$ | 45(2) | 67(3) | 95(4) | −3(2) | −15(3) | −6(3) |
| C$_{3f}$ | 59(3) | 34(2) | 78(3) | −2(2) | −6(3) | −9(2) |
| C$_{4f}$ | 45(2) | 23(2) | 48(2) | 7(1) | 6(2) | −1(1) |
| O$_{1g}$ | 34(1) | 41(1) | 37(1) | 19(1) | 7(1) | −1(1) |
| C$_{1g}$ | 31(2) | 56(2) | 50(2) | 20(2) | 4(2) | −5(2) |
| C$_{2g}$ | 47(3) | 65(3) | 72(3) | 35(2) | 2(2) | −12(2) |
| C$_{3g}$ | 60(3) | 75(3) | 50(2) | 36(2) | 16(2) | −8(2) |
| C$_{4g}$ | 45(2) | 77(3) | 35(2) | 27(2) | 8(2) | −5(2) |

[a] The numbers in parentheses are the estimated standard deviations in the last significant digit.
[b] The form of the anisotropic thermal parameter is given in reference 8 on page 6 of the structure report.
[c] Atoms are labeled in agreement with FIG. 1.

TABLE III

Atomic Coordinates for Hydrogen Atoms in Crystalline $[Cr_5(NC_4H_4)_{10}(OC_4H_8)_4]^a$

| Atom Type[b] | Fractional Coordinates $10^4x$ | $10^4y$ | $10^4z$ |
|---|---|---|---|
| H$_{1a}$ | −2129 | −661 | 1707 |
| H$_{2a}$ | −4154 | −55 | 1219 |
| H$_{3a}$ | −3608 | 1937 | −69 |
| H$_{4a}$ | −1267 | 2508 | −339 |
| H$_{1b}$ | 1053 | 3405 | −617 |
| H$_{2b}$ | 3405 | 4593 | −834 |
| H$_{3b}$ | 4676 | 3202 | 189 |
| H$_{4b}$ | 3031 | 1158 | 1020 |
| H$_{1c}$ | 1013 | 3445 | 3687 |
| H$_{2c}$ | 364 | 5592 | 3881 |
| H$_{3c}$ | −1331 | 5685 | 2512 |
| H$_{4c}$ | −1704 | 3580 | 1540 |
| H$_{1d}$ | 1881 | 1460 | 3743 |
| H$_{2d}$ | 3177 | −88 | 3396 |
| H$_{3d}$ | 1807 | −1790 | 2120 |
| H$_{4d}$ | −291 | −1252 | 1752 |
| H$_{1e}$ | −446 | −1976 | 3968 |
| H$_{2e}$ | −1997 | −4161 | 4742 |
| H$_{3e}$ | −4139 | −3699 | 4803 |
| H$_{4e}$ | −3678 | −1286 | 4012 |
| H$_{1fa}$ | 3351 | 3836 | 3136 |
| H$_{1fb}$ | 3882 | 3308 | 2299 |
| H$_{2fa}$ | 5068 | 5771 | 2893 |
| H$_{2fb}$ | 4965 | 5524 | 1806 |
| H$_{3fa}$ | 3462 | 6711 | 2728 |
| H$_{3fb}$ | 4068 | 7245 | 1757 |
| H$_{4fa}$ | 2417 | 5653 | 964 |
| H$_{4fb}$ | 1641 | 5625 | 1839 |
| H$_{1ga}$ | −3631 | 2231 | 2623 |
| H$_{1gb}$ | −4455 | 813 | 3162 |
| H$_{2ga}$ | −5037 | 2381 | 3901 |
| H$_{2gb}$ | −3704 | 3640 | 3750 |
| H$_{3ga}$ | −4129 | 1385 | 5124 |
| H$_{3gb}$ | −3307 | 3025 | 5266 |
| H$_{4ga}$ | −2173 | 1220 | 5050 |
| H$_{4gb}$ | −1565 | 2846 | 4703 |

[a] Hydrogen atoms were included in the structure factor calculations as idealized atoms (assuming sp$^2$- or sp$^3$- hybridization of the carbon atoms and a C—H bond length of 0.96Å) "riding" on their respective carbon atoms. The isotropic thermal parameter of each hydrogen atom was fixed at 1.2 times the equivalent isotropic thermal parameter of the carbon atom to which it is covalently bonded.
[b] Hydrogen atoms are labeled with the same numerical and literal subscripts as their carbon atoms with an additional literal subscript (a or b) where necessary to distinguish between hydrogen atoms bonded to the same carbon.

TABLE IV

Bond Lengths Involving Nonhydrogen Atoms in Crystalline $[Cr_5(NC_4H_4)_{10}(OC_4H_8)_4]^a$

| Type[b] | Length, Å | Type[b] | Length, Å |
|---|---|---|---|
| Cr$_1$ ... Cr$_2$ | 3.066(1) | O$_{1f}$—C$_{1f}$ | 1.451(5) |
| Cr$_2$ ... Cr$_3$ | 3.121(1) | O$_{1f}$—C$_{4f}$ | 1.453(5) |
| | | O$_{1g}$—C$_{1g}$ | 1.448(6) |
| Cr$_1$—N$_{1a}$ | 2.153(3) | O$_{1g}$—C$_{4g}$ | 1.451(5) |
| Cr$_1$—N$_{1b}$ | 2.092(3) | | |
| Cr$_2$—N$_{1a}$ | 2.178(3) | C$_{1a}$—C$_{2a}$ | 1.360(6) |
| Cr$_2$—N$_{1b}$ | 2.149(3) | C$_{2a}$—C$_{3a}$ | 1.395(6) |
| Cr$_2$—N$_{1c}$ | 2.112(4) | C$_{3a}$—C$_{4a}$ | 1.351(6) |
| Cr$_3$—N$_{1c}$ | 2.172(3) | C$_{1b}$—C$_{2b}$ | 1.338(6) |
| Cr$_3$—N$_{1d}$ | 2.101(4) | C$_{2b}$—C$_{3b}$ | 1.393(7) |
| Cr$_3$—N$_{1e}$ | 2.037(3) | C$_{3b}$—C$_{4b}$ | 1.376(6) |
| | | C$_{1c}$—C$_{2c}$ | 1.365(7) |
| Cr$_2$—O$_{1f}$ | 2.082(2) | C$_{2c}$—C$_{3c}$ | 1.400(6) |
| Cr$_3$—O$_{1g}$ | 2.068(3) | C$_{3c}$—C$_{4c}$ | 1.356(6) |
| | | C$_{1d}$—C$_{2d}$ | 1.376(7) |
| N$_{1a}$—C$_{1a}$ | 1.399(4) | C$_{2d}$—C$_{3d}$ | 1.396(6) |
| N$_{1a}$—C$_{4a}$ | 1.397(5) | C$_{3d}$—C$_{4d}$ | 1.367(8) |
| N$_{1b}$—C$_{1b}$ | 1.398(5) | C$_{1e}$—C$_{2e}$ | 1.370(5) |
| N$_{1b}$—C$_{4b}$ | 1.379(6) | C$_{2e}$—C$_{3e}$ | 1.374(8) |
| N$_{1c}$—C$_{1c}$ | 1.388(4) | C$_{3e}$—C$_{4e}$ | 1.366(6) |
| N$_{1c}$—C$_{4c}$ | 1.394(6) | | |
| N$_{1d}$—C$_{1d}$ | 1.349(5) | C$_{1f}$—C$_{2f}$ | 1.460(6) |
| N$_{1d}$—C$_{4d}$ | 1.377(5) | C$_{2f}$—C$_{3f}$ | 1.474(9) |
| N$_{1e}$—C$_{1e}$ | 1.370(6) | C$_{3f}$—C$_{4f}$ | 1.496(6) |
| N$_{1e}$—C$_{4e}$ | 1.361(6) | C$_{1g}$—C$_{2g}$ | 1.496(8) |
| | | C$_{2g}$—C$_{3g}$ | 1.485(7) |
| | | C$_{3g}$—C$_{4g}$ | 1.476(9) |

[a] The numbers in parentheses are the estimated standard deviations in the last significant digit.
[b] Atoms are labeled in agreement with FIG. 1.

TABLE V

Bond Angles Involving Nonhydrogen Atoms in Crystalline
$[Cr_5(MC_4H_4)_{10}(OC_4H_8)_4]^a$

| Type[b] | Angle, deg | Type[b] | Angle, deg |
|---|---|---|---|
| $N_{1a}Cr_1N_{1b}$ | 84.8(1) | $Cr_1N_{1a}Cr_2$ | 90.2(1) |
| $N_{1a}Cr_1N_{1a'}$[c] | 180.0(—)[d] | $Cr_1N_{1a}C_{1a}$ | 121.2(2) |
| $N_{1b}Cr_1N_{1a'}$[c] | 95.2(1) | $Cr_2N_{1a}C_{1a}$ | 118.0(2) |
| $N_{1b}Cr_1N_{1b'}$[c] | 180.0(—)[d] | $Cr_1N_{1a}C_{4a}$ | 113.4(2) |
| | | $Cr_2N_{1a}C_{4a}$ | 110.6(2) |
| $N_{1a}Cr_2N_{1b}$ | 82.9(1) | $C_{1a}N_{1a}C_{4a}$ | 103.5(3) |
| $N_{1a}Cr_2N_{1c}$ | 96.5(1) | $Cr_1N_{1b}Cr_2$ | 92.6(1) |
| $N_{1b}Cr_2N_{1c}$ | 168.9(1) | $Cr_1N_{1b}C_{1b}$ | 117.9(2) |
| $N_{1a}Cr_2O_{1f}$ | 162.4(1) | $Cr_2N_{1b}C_{1b}$ | 107.6(3) |
| $N_{1b}Cr_2O_{1f}$ | 89.5(1) | $Cr_1N_{1b}C_{4b}$ | 120.6(3) |
| $N_{1c}Cr_2O_{1f}$ | 87.9(1) | $Cr_2N_{1b}C_{4b}$ | 113.0(3) |
| | | $C_{1b}N_{1b}C_{4b}$ | 104.4(3) |
| $N_{1c}Cr_3N_{1d}$ | 88.1(1) | $Cr_2N_{1c}Cr_3$ | 93.5(1) |
| $N_{1c}Cr_3N_{1e}$ | 176.5(1) | $Cr_2N_{1c}C_{1c}$ | 121.4(3) |
| $N_{1d}Cr_3N_{1e}$ | 93.5(1) | $Cr_3N_{1c}C_{1c}$ | 100.0(2) |
| $N_{1c}Cr_3O_{1g}$ | 88.8(1) | $Cr_2N_{1c}C_{4c}$ | 116.1(2) |
| $N_{1d}Cr_3O_{1g}$ | 170.4(1) | $Cr_3N_{1c}C_{4c}$ | 121.5(2) |
| $N_{1e}Cr_3O_{1g}$ | 89.1(1) | $C_{1c}N_{1c}C_{4c}$ | 104.2(3) |
| | | $Cr_3N_{1d}C_{1d}$ | 121.3(3) |
| $N_{1a}C_{1a}C_{2a}$ | 110.6(3) | $Cr_3N_{1d}C_{4d}$ | 127.8(3) |
| $C_{1a}C_{2a}C_{3a}$ | 107.5(4) | $C_{1d}N_{1d}C_{4d}$ | 106.4(4) |
| $C_{2a}C_{3a}C_{4a}$ | 106.9(4) | $Cr_3N_{1e}C_{1e}$ | 126.3(3) |
| $C_{3a}C_{4a}N_{1a}$ | 111.5(3) | $Cr_3N_{1e}C_{4e}$ | 128.3(3) |
| $N_{1b}C_{1b}C_{2b}$ | 111.2(4) | $C_{1e}N_{1e}C_{4e}$ | 105.3(3) |
| $C_{1b}C_{2b}C_{3b}$ | 107.4(4) | | |
| $C_{2b}C_{3b}C_{4b}$ | 107.0(4) | $Cr_2O_1C_{1f}$ | 131.5(2) |
| $C_{3b}C_{4b}N_{1b}$ | 110.1(4) | $Cr_2O_{1f}C_{4f}$ | 118.9(2) |
| $N_{1c}C_{1c}C_{2c}$ | 110.9(4) | $C_{1f}O_{1f}C_{4f}$ | 109.1(3) |
| $C_{1c}C_{2c}C_{3c}$ | 106.8(4) | $Cr_3O_{1g}C_{1g}$ | 131.9(3) |
| $C_{2c}C_{3c}C_{4c}$ | 107.2(4) | $Cr_3O_{1g}C_{4g}$ | 118.6(3) |
| $C_{3c}C_{4c}N_{1c}$ | 110.9(3) | $C_{1g}O_{1g}C_{4g}$ | 109.5(4) |
| $N_{1d}C_{1d}C_{2d}$ | 110.3(4) | | |
| $C_{1d}C_{2d}C_{3d}$ | 106.7(4) | $O_1C_{1f}C_{2f}$ | 105.0(4) |
| $C_{2d}C_{3d}C_{4d}$ | 106.6(5) | $C_{1f}C_{2f}C_{3f}$ | 104.9(4) |
| $C_{3d}C_{4d}N_{1d}$ | 109.9(3) | $C_{2f}C_{3f}C_{4f}$ | 104.4(4) |
| $N_{1e}C_{1e}C_{2e}$ | 110.0(4) | $C_{3f}C_{4f}O_{1f}$ | 105.4(4) |
| $C_{1e}C_{2e}C_{3e}$ | 107.2(4) | $O_{1g}C_{1g}C_{2g}$ | 104.8(4) |
| $C_{2e}C_{3e}C_{4e}$ | 106.7(4) | $C_{1g}C_{2g}C_{3g}$ | 104.2(5) |
| $C_{3e}C_{4e}N_{1e}$ | 110.8(5) | $C_{2g}C_{3g}C_{4g}$ | 104.2(4) |
| | | $C_{3g}C_{4g}O_{1g}$ | 106.1(4) |

[a]The numbers in parentheses are the estimated standard deviations in the last significant digit.
[b]Atoms are labeled in agreement with FIG. 1
[c]Atoms labeled with a prime ( ) are related to nonprimed atoms by the symmetry operation -x, -y, -z where the fractional coordinates (x, y, z) are given in Table I.
[d]This is a symmetry-required value and is therefore listed without an estimated standard deviation.

EXAMPLE V

Figure 3:
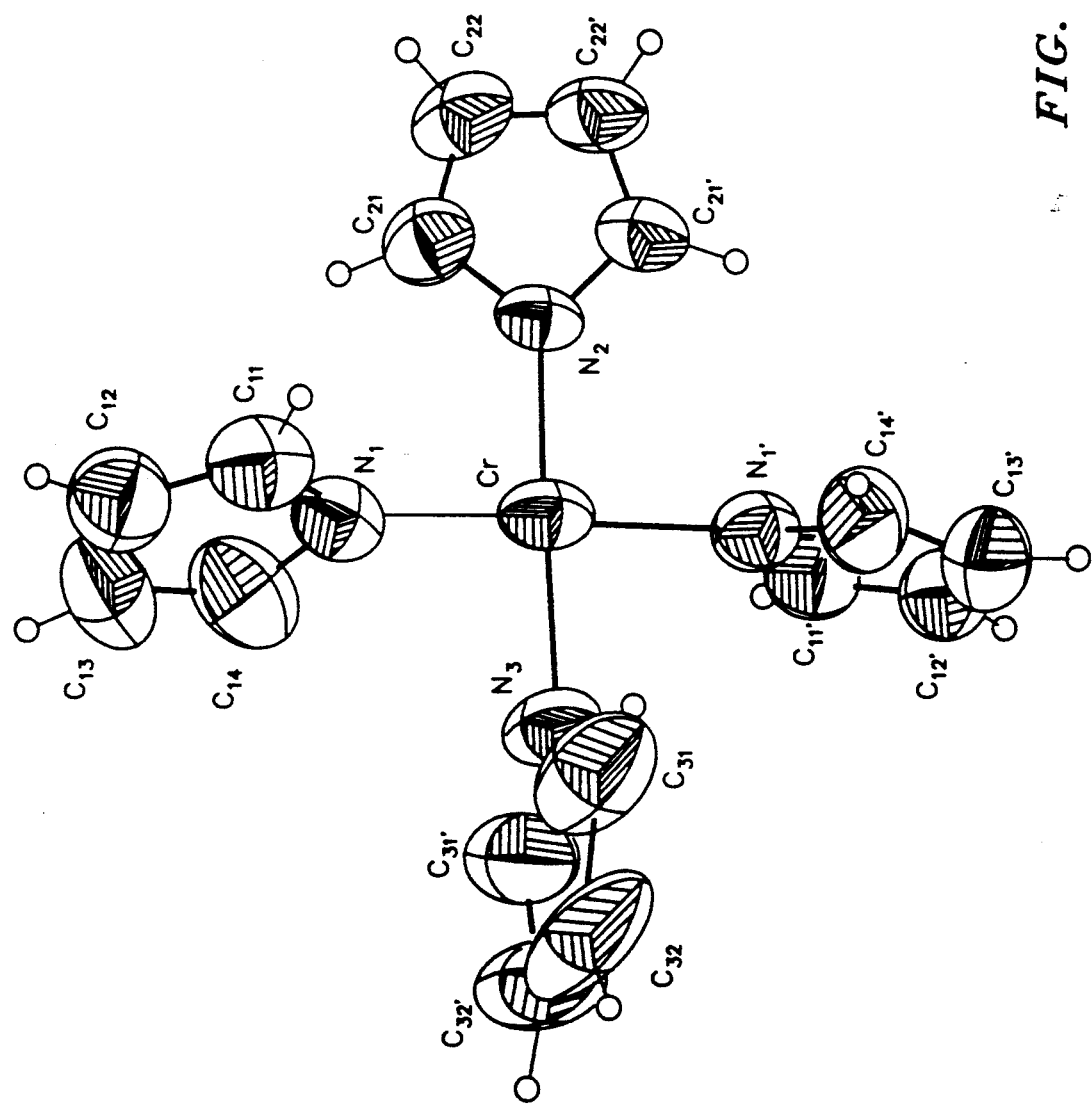
FIG. 3 is a computer generated ORTEP drawing of the structure, or a simplified structural representation or formula, of a molecule of Product III, $[Cr(NC_4H_4)_4]^{-2}$, as determined by single crystal x-ray crystallography.

A single crystal x-ray structure was obtained for $Cr(NC_4H_4)_4$, a portion of Product III and shown in FIG. 3. A single crystal x-ray structure was obtained for $[Na]_2[Cr(NC_4H_4)_4] \cdot 2(OC_4H_8)$, Product III and shown in FIG. 4. The description of the single-crystal sample and mounting used for the data collection are as follows:
 Color: Red-Orange
 Shape: Rectangular parallelepiped
 Dimensions: 0.50×0.55×0.65 mm
 Crystal Mount: Crystal was glued to the inside of a thin-walled glass capillary and sealed under $N_2$.
 Crystal Orientation: Crystal was oriented with its longest edge nearly parallel to the phi axis of the diffractometer.
 Width at Half-height from ω Scans: 0.86°
The space group and cell data are as follows:
 Crystal System: Monoclinic
 Space Group and Number:[2] C2/c - $C_{2h}^6$ (no. 15)
 Number of Computer-Centered Reflections Used in the Least-Squares Refinement of the Cell Dimensions:
 Dimensions: 15 20°>25°, °C.=20°+1°
Lattice Constants with esd's:

| a = 9.522(2)Å | α = 90.00° | V = 2697(1)Å³ |
|---|---|---|
| b = 15.118(2)Å | β = 98.99(1)° | Z = 4 |
| c = 18.967(3)Å | γ = 90.00° | λ = 0.71073Å |

Molecular Weight: 506.52 amu
Calculated Density: 1.248 g/cm⁻³
Linear Absorption Coefficient:[3a] 0.47 mm⁻¹
Tables VI-X list the resultant parameters used to generate the molecular structures shown in FIGS. 3 and 4.

TABLE VI

Atomic Coordinates for Nonhydrogen Atoms in Crystalline
${Na}_2{Cr(NC_4H_4)_4}-2(OC_4H_8)^a$

| Atom Type[b] | Fractional Coordinates | | | Equivalent Isotropic Thermal Parameter, B, Å² × 10[c] |
|---|---|---|---|---|
| | $10^4x$ | $10^4y$ | $10^4z$ | |
| Anion | | | | |
| Cr | 0[d] | 2982(1) | 2500[d] | 50(1) |
| $N_1$ | 1901(4) | 2924(2) | 3183(2) | 56(1) |
| $N_2$ | 0[d] | 4343(3) | 2500[d] | 52(1) |
| $N_3$ | 0[d] | 1612(3) | 2500[d] | 70(2) |
| $C_{11}$ | 3241(5) | 2950(3) | 3000(3) | 65(2) |
| $C_{12}$ | 4224(6) | 2769(3) | 3587(3) | 73(2) |
| $C_{13}$ | 3513(7) | 2630(4) | 4146(3) | 82(2) |
| $C_{14}$ | 2094(7) | 2734(4) | 3884(3) | 76(2) |
| $C_{21}$ | 907(5) | 4884(3) | 2926(3) | 60(1) |
| $C_{22}$ | 582(4) | 5753(3) | 2766(3) | 69(2) |
| $C_{31}$ | 390(5) | 1081(3) | 1996(4) | 94(2) |
| $C_{32}$ | 236(7) | 213(3) | 2189(5) | 133(6) |
| Cation | | | | |
| Na | 2301(2) | 6079(1) | 1783(1) | 69(1) |
| Solvent of Crystallization | | | | |
| $O_1$ | 2065(4) | 5108(2) | 830(2) | 83(1) |
| $C_{41}$ | 2759(11) | 5174(5) | 239(4) | 143(4) |
| $C_{42}$ | 2804(11) | 4319(5) | −79(4) | 148(4) |
| $C_{43}$ | 1893(10) | 3786(5) | 264(5) | 142(4) |
| $C_{44}$ | 1699(9) | 4231(4) | 902(4) | 120(3) |

[a]The numbers in parentheses are the estimated standard deviations in the last significant digit.
[b]Atoms are labeled in agreement with FIGS. 3 and 4.
[c]This is one-third of the trace of the orthogonalized $B_{ij}$ tensor.
[d]This is a symmetry-required value and is therefore listed without an estimated standard deviation.

TABLE VII

Anisotropic Thermal Parameters 0$^{Nonhydrogen}$
Atoms in Crystalline
${Na}_2{Cr(NC_4H_4)_4}-2OC_4H_8^{a,b}$

| Atom Type[c] | Anisotropic Thermal Parameter (Å² × 10) | | | | | |
|---|---|---|---|---|---|---|
| | $B_{11}$ | $B_{22}$ | $B_{33}$ | $B_{12}$ | $B_{13}$ | $B_{23}$ |
| Anion | | | | | | |
| Cr | 64(1) | 34(1) | 55(1) | [d] | 15(1) | 0[d] |
| $N_1$ | 69(2) | 44(2) | 56(2) | 6(1) | 12(1) | 6(1) |
| $N_2$ | 64(3) | 39(2) | 56(3) | 0[d] | 16(2) | 0[d] |
| $N_3$ | 65(3) | 38(2) | 107(4) | 0[d] | 14(3) | 0[d] |
| $C_{11}$ | 79(3) | 50(2) | 70(3) | −6(2) | 18(2) | 2(2) |
| $C_{12}$ | 70(3) | 62(3) | 84(3) | 4(2) | 7(2) | −8(2) |
| $C_{13}$ | 103(4) | 79(3) | 58(3) | 22(3) | −8(3) | 8(2) |
| $C_{14}$ | 86(3) | 86(3) | 58(3) | 16(3) | 16(2) | 5(2) |
| $C_{21}$ | 66(2) | 45(2) | 70(3) | −2(2) | 15(2) | −6(2) |
| $C_{22}$ | 68(3) | 38(2) | 105(4) | −7(2) | 27(2) | −9(2) |
| $C_{31}$ | 65(3) | 61(3) | 152(5) | 6(2) | 9(3) | −36(3) |
| $C_{32}$ | 71(5) | 46(2) | 266(15) | 6(3) | −20(6) | −44(4) |
| Cation | | | | | | |
| Na | 70(1) | 57(1) | 81(1) | −2(1) | 15(1) | −15(1) |
| Solvent of Crystallization | | | | | | |
| $O_1$ | 100(2) | 65(2) | 82(2) | −10(2) | 30(2) | −16(2) |
| $C_{41}$ | 222(8) | 112(5) | 116(5) | −46(5) | 92(6) | −22(4) |
| $C_{42}$ | 192(8) | 160(8) | 107(5) | 12(6) | 70(5) | −32(5) |
| $C_{43}$ | 147(6) | 109(6) | 177(8) | −27(5) | 48(6) | −69(6) |

TABLE VII-continued

Anisotropic Thermal Parameters $O^{Nonhydrogen}$ Atoms in Crystalline
$\{Na\}_2\{Cr(NC_4H_4)_4\}-2OC_4H_8$ [a,b]

| Atom Type[c] | Anisotropic Thermal Parameter ($Å^2 \times 10$) | | | | | |
|---|---|---|---|---|---|---|
| | $B_{11}$ | $B_{22}$ | $B_{33}$ | $B_{12}$ | $B_{13}$ | $B_{23}$ |
| $C_{44}$ | 177(6) | 77(4) | 124(5) | −21(4) | 76(5) | −14(3) |

[a] The numbers in parentheses are the estimated standard deviations in the last significant digit.
[b] The form of the anisotropic thermal parameter is given in reference 8 on page 6 of the structure report.
[c] Atoms are labeled in agreement with FIGS. 3 and 4.
[d] This is a symmetry-required value and is therefore listed without an estimated standard deviation.

TABLE VIII

Atomic Coordinates for Hydrogen Atoms in Crystalline $\{Na\}_2\{Cr(NC_4H_4)_4\}-2(OC_4H_8)$ [a]

| Atom Type[b] | Fractional Coordinates | | |
|---|---|---|---|
| | $10^4x$ | $10^4y$ | $10^4z$ |
| *Anion* | | | |
| $H_{11}$ | 3456 | 3081 | 2541 |
| $H_{12}$ | 5235 | 2748 | 3680 |
| $H_{13}$ | 3922 | 2488 | 4628 |
| $H_{14}$ | 1341 | 2679 | 4164 |
| $H_{21}$ | 1665 | 4687 | 3285 |
| $H_{22}$ | 1071 | 6262 | 2985 |
| $H_{31}$ | 706 | 1274 | 1565 |
| $H_{32}$ | 493 | −301 | 1937 |
| *Solvent of Crystallization* | | | |
| $H_{41a}$ | 2250 | 5576 | −100 |
| $H_{41b}$ | 3710 | 5388 | 385 |
| $H_{42a}$ | 3756 | 4091 | −1 |
| $H_{42b}$ | 2464 | 4348 | −583 |
| $H_{43a}$ | 995 | 3707 | −39 |
| $H_{43b}$ | 2326 | 3220 | 377 |
| $H_{44a}$ | 2295 | 3973 | 1304 |
| $H_{44b}$ | 723 | 4191 | 969 |

[a] Hydrogen atoms were included in the structure factor calculations as idealized atoms (assuming sp²- or sp³-hybridization of the carbon atoms and a C—H bond length of 0.96Å) "riding" on their respective carbon atoms. The isotropic thermal parameter of each hydrogen atom was fixed at 1.2 times the equivalent isotropic thermal parameter of the carbon atom to which it is covalently bonded.
[b] Hydrogen atoms are labeled with the same numerical subscripts as the carbon atoms to which they are covalently bonded with an additional literal subscript (a or b) where necessary to distinguish between hydrogens bonded to the same carbon.

TABLE IX

Anion Bond Lengths and Bond Angles Involving Nonhydrogen Atoms in Crystalline $\{Na\}_2\{Cr(NC_4H_4)_4\}-2OC_4H_8$ [a]

| Type[b] | Length, Å | Type[b] | Length, Å |
|---|---|---|---|
| $Cr-N_1$ | 2.057(3) | $C_{11}-C_{12}$ | 1.355(7) |
| $Cr-N_2$ | 2.056(4) | $C_{12}-C_{13}$ | 1.361(9) |
| $Cr-N_3$ | 2.072(5) | $C_{13}-C_{14}$ | 1.374(9) |
| | | $C_{21}-C_{22}$ | 1.372(6) |
| $N_1-C_{11}$ | 1.369(7) | $C_{22}-C_{22'}$[c] | 1.379(9) |
| $N_1-C_{14}$ | 1.344(6) | $C_{31}-C_{32}$ | 1.376(7) |
| $N_2-C_{21}$ | 1.360(5) | $C_{32}-C_{32'}$[c] | 1.327(18) |
| $N_3-C_{31}$ | 1.344(7) | | |

| Type[b] | Angle, deg. | Type[b] | Angle, deg. |
|---|---|---|---|
| $N_1CrN_2$ | 92.5(1) | $N_1C_{11}C_{12}$ | 110.5(5) |
| $N_1CrN_3$ | 87.5(1) | $C_{11}C_{12}C_{13}$ | 107.3(5) |
| $N_1CrN_{1'}$[c] | 175.1(2) | $C_{12}C_{13}C_{14}$ | 106.4(5) |
| $N_2CrN_3$ | 180.0(−)[d] | $N_1C_{14}C_{13}$ | 110.9(5) |
| | | $N_2C_{21}C_{22}$ | 110.2(4) |
| $CrN_1C_{11}$ | 127.5(3) | $C_{21}C_{22}C_{22'}$[c] | 106.8(3) |
| $CrN_1C_{14}$ | 127.1(4) | $N_3C_{31}C_{32}$ | 109.1(6) |
| $C_{11}N_1C_{14}$ | 104.9(4) | $C_{31}C_{32}C_{32'}$[c] | 107.5(5) |
| $CrN_2C_{21}$ | 127.0(2) | | |
| $C_{21}N_2C_{21'}$[c] | 106.0(5) | | |
| $CrN_3C_{31}$ | 126.7(3) | | |

TABLE IX-continued

Anion Bond Lengths and Bond Angles Involving Nonhydrogen Atoms in Crystalline $\{Na\}_2\{Cr(NC_4H_4)_4\}-2OC_4H_8$ [a]

| | |
|---|---|
| $C_{31}N_3C_{31'}$[c] | 106.7(6) |

[a] The numbers in parentheses are the estimated standard deviations in the last significant digit.
[b] Atoms are labeled in agreement with FIG. 4.
[c] Atoms labeled with a prime(') are related to nonprimed atoms by the symmetry operation -x,y,½-x.

TABLE X

Bond Lengths and Angles Involving the Nonhydrogen Atoms of the Cation and Solvent of Crystallization in $\{Na\}_2\{Cr(NC_4H_4)_4\}-2(OC_4H_8)$ [a]

| Type[b] | Length, Å | Type[b] | Length, Å |
|---|---|---|---|
| $Na-O_1$ | 2.313(4) | $O_1-C_{41}$ | 1.390(10) |
| | | $O_1-C_{44}$ | 1.38(7) |
| $Na...N_{1''}$[c] | 2.888(4) | | |
| $Na...N_{3''}$[c] | 2.830(4) | $C_{41}-C_{42}$ | 1.43(1) |
| | | $C_{42}-C_{43}$ | 1.42(1) |
| | | $C_{43}-C_{44}$ | 1.42(1) |

| Type[b] | Angle, deg. | Type[b] | Angle, deg. |
|---|---|---|---|
| $O_1NaN_{1''}$[c] | 128.6(3) | $C_{41}O_1C_{44}$ | 107.9(5) |
| $O_1NaN_{3''}$[c] | 121.8(3) | | |
| $N_{1''}NaN_{3''}$[c] | 59.9(3) | $O_1C_{41}C_{42}$ | 109.0(7) |
| | | $C_{41}C_{42}C_{43}$ | 105.0(8) |
| $NaO_1C_{41}$ | 125.7(4) | $C_{42}C_{43}C_{44}$ | 107.0(7) |
| $NaO_1C_{44}$ | 121.8(4) | $O_1C_{44}C_{43}$ | 107.6(7) |

[a] The numbers in parentheses are the estimated standard deviations in the last significant digit.
[b] Atoms are labeled in agreement with FIG. 4.
[c] Atoms labeled with a double prime('') are related to nonprimed atoms by the symmetry operation ½ − x, ½ + y, ½ − z.

EXAMPLE VI

Single crystal x-ray structures were obtained for $[Cr(NC_4H_4)_5(OC_4H_8)]$, shown in FIG. 5, and $[Cr(NC_4H_4)_5(OC_4H_8)][Na]_2.4(OC_4H_8)$, Product IV, and shown in FIG. 6. The description of the single-crystal sample and mounting used for data collection are as follows:

Color: Purple
Shape: Rectangular parallelepiped
Dimensions: 0.50×0.55×0.63 mm
Crystal Mount: Crystal was glued to the inside of a thin-walled glass capillary and sealed under $N_2$.
Crystal Orientation: Crystal was oriented with its longest edge nearly parallel to the phi axis of the diffractometer.
Width at Half-height from ω Scans: 0.42°
The space group and cell data are as follows:
Crystal System: Monoclinic
Space Group and Number:[2] $P2_1$-$C_2^2$(No. 4)
Number of Computer-Centered Reflections Used in the Least-Squares
Refinement of the Cell Dimensions: 15 20°>20°, °C.=20±1°
Lattice Constants with esd's:

| | | |
|---|---|---|
| a = 10.042(2)Å | α = 90.00° | V = 2162(1)Å³ |
| b = 17.242(4)Å | β = 106.54(2)° | Z = 2 |
| c = 13.025(3)Å | γ = 90.00° | λ = 0.71073Å |

Molecular Weight=788.93 amu
Calculated Density: 1.212 g/cn⁻³
Linear Absorption Coefficient:[3a] 0.32 mm⁻¹

Tables XI-XV list the resultant parameters used to generate the molecular structures shown in FIGS. 5 and 6.

TABLE XI

Atomic Coordinates for Nonhydrogen Atoms in Crystalline [Cr(NC$_4$H$_4$)$_5$(OC$_4$H$_8$)][Na]$_2$—4(OC$_4$H$_8$)[a]

| Atom Type[b] | Fractional Coordinates | | | Equivalent Isotropic Thermal Parameter, B, Å$^2$ × 10[c] |
|---|---|---|---|---|
| | 10$^4$x | 10$^4$y | 10$^4$z | |
| Anion | | | | |
| Cr | 198(1) | 1477 | 2531(1) | 32(1) |
| N$_{1a}$ | 1694(5) | 2026(3) | 2028(4) | 40(2) |
| C$_{1a}$ | 1749(7) | 2782(4) | 1742(6) | 48(2) |
| C$_{2a}$ | 2929(8) | 2926(5) | 1420(7) | 66(3) |
| C$_{3a}$ | 3661(7) | 2236(5) | 1554(6) | 62(3) |
| C$_{4a}$ | 2899(6) | 1695(5) | 1913(5) | 52(2) |
| N$_{1b}$ | 1651(5) | 1087(3) | 3885(4) | 40(2) |
| C$_{1b}$ | 1463(8) | 560(4) | 4575(5) | 48(2) |
| C$_{2b}$ | 2572(9) | 518(6) | 5423(8) | 82(4) |
| C$_{3b}$ | 3554(8) | 1064(5) | 5275(6) | 70(3) |
| C$_{4b}$ | 2952(6) | 1382(5) | 4340(5) | 48(2) |
| N$_{1c}$ | −1326(5) | 1888(3) | 1250(4) | 38(2) |
| C$_{1c}$ | −1200(8) | 2172(4) | 266(6) | 51(2) |
| C$_{2c}$ | −2458(8) | 2270(5) | −476(6) | 58(3) |
| C$_{3c}$ | −3435(8) | 2038(6) | 56(7) | 75(3) |
| C$_{4c}$ | −2710(7) | 1826(5) | 1091(6) | 56(3) |
| N$_{1d}$ | −32(5) | 2455(4) | 3445(5) | 43(2) |
| C$_{1d}$ | 504(7) | 2562(5) | 4505(6) | 49(2) |
| C$_{2d}$ | 107(9) | 3278(5) | 4774(7) | 72(3) |
| C$_{3d}$ | −698(8) | 3629(5) | 3832(6) | 59(3) |
| C$_{4d}$ | −769(7) | 3108(4) | 3055(6) | 52(2) |
| N$_{1e}$ | 315(5) | 505(4) | 1690(4) | 40(2) |
| C$_{1e}$ | −574(8) | 277(5) | 704(6) | 55(3) |
| C$_{2e}$ | −197(10) | −432(5) | 403(7) | 67(3) |
| C$_{3e}$ | 990(10) | −662(6) | 1256(8) | 79(4) |
| C$_{4e}$ | 1265(8) | −92(4) | 2016(7) | 51(3) |
| O$_{1f}$ | −1356(4) | 926(3) | 3083(4) | 43(1) |
| C$_{1f}$ | −2047(7) | 1244(5) | 3800(6) | 57(3) |
| C$_{2f}$ | −3263(10) | 713(6) | 3706(9) | 98(5) |
| C$_{3f}$ | −2833(11) | −21(6) | 3402(8) | 93(4) |
| C$_{4f}$ | −1903(8) | 171(5) | 2724(7) | 64(3) |
| Cation 1 | | | | |
| Na$_1$ | 2254(3) | 3336(2) | 3737(3) | 75(1) |
| Cation 2 | | | | |
| Na$_2$ | 1430(3) | 974(2) | 126(2) | 62(1) |
| Solvent Molecules of Crystallization | | | | |
| O$_{1g}$ | 4576(6) | 3329(4) | 4706(5) | 83(2) |
| C$_{1g}$ | 5748(9) | 3100(10) | 4433(9) | 125(6) |
| C$_{2g}$ | 6723(12) | 2831(11) | 5281(9) | 145(7) |
| C$_{3g}$ | 6503(15) | 3272(11) | 6146(11) | 204(8) |
| C$_{4g}$ | 5037(14) | 3498(11) | 5737(10) | 170(8) |
| O$_{1h}$ | 2342(7) | 4602(4) | 3279(6) | 97(3) |
| C$_{1h}$ | 1316(11) | 5151(7) | 2894(10) | 112(5) |
| C$_{2h}$ | 2017(16) | 5830(9) | 2541(11) | 153(7) |
| C$_{3h}$ | 3180(12) | 5561(10) | 2425(10) | 131(6) |
| C$_{4h}$ | 3551(13) | 4848(7) | 3070(11) | 115(6) |
| O$_{1i}$ | 1391(7) | 1752(4) | −1377(4) | 80(2) |
| C$_{1i}$ | 2235(19) | 1594(11) | −1998(13) | 160(8) |
| C$_{2i}$ | 2716(17) | 2287(14) | −2337(15) | 165(10) |
| C$_{3i}$ | 1991(28) | 2906(11) | −1934(14) | 204(12) |
| C$_{4i}$ | 1010(16) | 2533(7) | −1523(9) | 128(6) |
| O$_{1j}$ | 3037(5) | 155(4) | −264(5) | 72(2) |
| C$_{1j}$ | 4389(10) | 48(7) | 427(5) | 113(5) |
| C$_{2j}$ | 4998(16) | −571(10) | −23(16) | 174(8) |
| C$_{3j}$ | 4001(11) | −840(8) | −1006(10) | 127(6) |
| C$_{4j}$ | 2728(11) | −493(7) | −974(8) | 92(4) |

[a]The numbers in parentheses are the estimated standard deviations in the last significant digit.
[b]Atoms are labeled in agreement with FIGS. 5 and 6.
[c]This is one-third of the trace of the orthogonalized B$_{ij}$ tensor.

TABLE XII

Anisotropic Thermal Parameters Nonhydrogen Atoms in Crystalline [Cr(NC$_4$H$_4$)$_5$(OC$_4$H$_8$)][Na]$_2$—4(OC$_4$H$_8$)[a,b]

| Atom Type[c] | Anisotropic Thermal Parameter (Å$^2$ × 10) | | | | | |
|---|---|---|---|---|---|---|
| | B$_{11}$ | B$_{22}$ | B$_{33}$ | B$_{12}$ | B$_{13}$ | B$_{23}$ |
| Anion | | | | | | |
| Cr | 29(1) | 31(1) | 38(1) | (1) | 12(1) | 1(1) |
| N$_{1a}$ | 33(2) | 44(3) | 44(3) | −1(2) | 11(2) | 5(2) |
| C$_{1a}$ | 48(4) | 37(3) | 59(4) | −0(3) | 15(3) | 3(3) |
| C$_{2a}$ | 55(4) | 61(5) | 90(5) | −19(4) | 34(4) | 13(4) |
| C$_{3a}$ | 37(3) | 82(6) | 76(5) | −9(3) | 33(3) | 2(4) |
| C$_{4a}$ | 40(3) | 64(5) | 52(4) | 4(3) | 16(3) | −5(3) |
| N$_{1b}$ | 36(2) | 44(3) | 36(3) | 7(2) | 5(2) | 12(2) |
| C$_{1b}$ | 52(4) | 51(4) | 40(3) | −1(3) | 9(3) | 10(3) |
| C$_{2b}$ | 73(5) | 85(6) | 83(6) | 2(5) | 13(4) | 44(5) |
| C$_{3b}$ | 51(4) | 88(6) | 54(4) | 0(4) | −13(3) | 12(4) |
| C$_{4b}$ | 41(3) | 55(4) | 45(3) | 0(3) | 5(2) | 4(4) |
| N$_{1c}$ | 33(2) | 41(3) | 39(3) | 4(2) | 9(2) | 1(2) |
| C$_{1c}$ | 52(4) | 51(4) | 51(4) | 6(3) | 16(3) | 5(3) |
| C$_{2c}$ | 64(5) | 62(5) | 37(4) | −1(4) | −4(3) | 4(4) |
| C$_{3c}$ | 32(3) | 92(6) | 89(6) | 4(4) | −3(4) | 29(5) |
| C$_{4c}$ | 42(3) | 78(5) | 48(4) | −1(3) | 9(3) | 14(4) |
| N$_{1d}$ | 31(2) | 44(3) | 56(3) | 4(2) | 13(2) | −1(3) |
| C$_{1d}$ | 44(3) | 60(5) | 39(4) | −5(3) | 8(3) | −11(3) |
| C$_{2d}$ | 63(4) | 70(6) | 84(6) | −11(4) | 20(4) | −47(5) |
| C$_{3d}$ | 69(4) | 43(4) | 73(5) | 9(3) | 32(4) | −14(4) |
| C$_{4d}$ | 42(3) | 53(4) | 63(4) | 8(3) | 17(3) | 3(4) |
| N$_{1e}$ | 47(3) | 36(3) | 39(3) | −3(2) | 17(2) | −7(2) |
| C$_{1e}$ | 59(4) | 49(4) | 53(4) | −15(3) | 11(3) | −1(4) |
| C$_{2e}$ | 92(5) | 48(4) | 69(5) | −20(4) | 36(4) | −26(4) |
| C$_{3e}$ | 91(6) | 45(5) | 106(7) | 4(4) | 37(5) | −13(5) |
| C$_{4e}$ | 62(4) | 23(4) | 69(5) | 7(3) | 20(4) | −7(3) |
| O$_{1f}$ | 40(2) | 42(2) | 51(2) | −4(2) | 20(2) | 2(2) |
| C$_{1f}$ | 61(4) | 64(5) | 60(4) | −2(3) | 39(3) | 4(4) |
| C$_{2f}$ | 81(6) | 95(7) | 144(8) | −24(5) | 74(6) | 1(6) |
| C$_{3f}$ | 109(7) | 80(6) | 117(7) | −26(5) | 75(6) | −3(6) |
| C$_{4f}$ | 61(4) | 53(4) | 85(5) | −27(4) | 30(4) | −16(4) |
| Cation 1 | | | | | | |
| Na$_1$ | 57(2) | 71(2) | 95(2) | −13(1) | 21(2) | −2(2) |
| Cation 2 | | | | | | |
| Na$_2$ | 68(2) | 69(2) | 56(2) | −2(1) | 30(1) | −3(2) |
| Solvent Molecules of Crystallization | | | | | | |
| O$_{1g}$ | 58(3) | 95(4) | 92(4) | −8(3) | 15(3) | −2(4) |
| C$_{1g}$ | 54(5) | 215(14) | 108(8) | 0(7) | 29(5) | −7(9) |
| C$_{2g}$ | 96(7) | 226(15) | 121(9) | 52(9) | 43(7) | 51(10) |
| C$_{3g}$ | 129(10) | 277(19) | 148(11) | 52(12) | −56(9) | −134(13) |
| C$_{4g}$ | 134(10) | 250(18) | 128(10) | 44(11) | 39(9) | −89(11) |
| O$_{1h}$ | 71(4) | 68(4) | 152(6) | −8(3) | 32(4) | −3(4) |
| C$_{1h}$ | 92(7) | 95(8) | 144(9) | −2(6) | 28(7) | −3(7) |
| C$_{2h}$ | 212(14) | 108(9) | 140(10) | 36(10) | 50(10) | 66(9) |
| C$_{3h}$ | 99(8) | 175(14) | 101(8) | −6(9) | −2(6) | 32(9) |
| C$_{4h}$ | 99(8) | 79(7) | 168(11) | −13(6) | 38(8) | 29(8) |
| O$_{1i}$ | 98(4) | 82(4) | 73(3) | 8(3) | 47(3) | 13(3) |
| C$_{1i}$ | 230(15) | 128(11) | 168(12) | 8(11) | 131(12) | 74(10) |
| C$_{2i}$ | 112(10) | 222(21) | 156(15) | 1(12) | 28(13) | 23(16) |
| C$_{3i}$ | 370(26) | 124(12) | 135(12) | −93(15) | 99(15) | 34(10) |
| C$_{4i}$ | 223(13) | 81(7) | 106(8) | 32(8) | 91(9) | 31(6) |
| O$_{1j}$ | 59(3) | 64(3) | 94(4) | 5(3) | 22(3) | −21(3) |
| C$_{1j}$ | 88(7) | 101(8) | 133(9) | 19(6) | 2(6) | −58(7) |
| C$_{2j}$ | 94(8) | 190(14) | 205(13) | 73(10) | −11(9) | −90(13) |
| C$_{3j}$ | 83(7) | 130(10) | 160(10) | 16(7) | 20(7) | −86(9) |
| C$_{4j}$ | 82(6) | 104(8) | 92(7) | −7(6) | 29(5) | −41(6) |

[a]The numbers in parentheses are the estimated standard deviations in the last significant digit.
[b]The form of the anisotropic thermal parameter is given in reference 8 on page 6 of the structure report.
[c]Atoms are labeled in agreement with FIGS. 5 and 6.

TABLE XIII

Atomic Coordinates for Hydrogen Atoms in Crystalline [Cr(NC$_4$H$_4$)$_5$(OC$_4$H$_8$)][Na]$_2$—4(OC$_4$N$_8$)[a]

| Atom Type[b] | Fractional Coordinates | | |
|---|---|---|---|
| | 10$^4$x | 10$^4$y | 10$^4$z |
| Anion | | | |
| H$_{1a}$ | 1061 | 3165 | 1756 |
| H$_{2a}$ | 3182 | 3406 | 1151 |
| H$_{3a}$ | 4547 | 2153 | 1428 |
| H$_{4a}$ | 3162 | 1162 | 2059 |
| H$_{1b}$ | 637 | 254 | 4479 |
| H$_{2b}$ | 2692 | 174 | 6022 |
| H$_{3b}$ | 4453 | 1179 | 5753 |

TABLE XIII-continued

Atomic Coordinates for Hydrogen Atoms in Crystalline
$[Cr(NC_4H_4)_5(OC_4H_8)][Na]_2 \cdot 4(OC_4N_8)^a$

| Atom Type[b] | Fractional Coordinates | | |
|---|---|---|---|
| | $10^4 x$ | $10^4 y$ | $10^4 z$ |
| $H_{4b}$ | 3373 | 1775 | 4016 |
| $H_{1c}$ | −326 | 2281 | 132 |
| $H_{2c}$ | −2637 | 2453 | −1199 |
| $H_{3c}$ | −4426 | 2031 | −243 |
| $H_{4c}$ | −3137 | 1655 | 1623 |
| $H_{1d}$ | 1070 | 2197 | 4997 |
| $H_{2d}$ | 349 | 3499 | 5480 |
| $H_{3d}$ | −1115 | 4135 | 3762 |
| $H_{4d}$ | −1278 | 3184 | 2317 |
| $H_{1e}$ | −1346 | 578 | 293 |
| $H_{2e}$ | −630 | −712 | −243 |
| $H_{3e}$ | 1503 | −1135 | 1285 |
| $H_{4e}$ | 1999 | −107 | 2676 |
| $H_{1fa}$ | −1447 | 1250 | 4520 |
| $H_{1fb}$ | −2359 | 1762 | 3588 |
| $H_{2fa}$ | −4069 | 899 | 3170 |
| $H_{2fb}$ | −3468 | 674 | 4380 |
| $H_{3fa}$ | −2341 | −312 | 4022 |
| $H_{3fb}$ | −3620 | −314 | 2996 |
| $H_{4fa}$ | −2417 | 184 | 1980 |
| $H_{4fb}$ | −1165 | −201 | 2831 |
| Solvent of Crystallization | | | |
| $H_{1ga}$ | 6103 | 3536 | 4135 |
| $H_{1gb}$ | 5503 | 2694 | 3909 |
| $H_{2ga}$ | 6629 | 2283 | 5371 |
| $H_{2gb}$ | 7629 | 2940 | 5209 |
| $H_{3ga}$ | 6644 | 2947 | 6766 |
| $H_{3gb}$ | 7102 | 3717 | 6322 |
| $H_{4ga}$ | 4960 | 4045 | 5839 |
| $H_{4gb}$ | 4493 | 3223 | 6118 |
| $H_{1ha}$ | 596 | 4950 | 2301 |
| $H_{1hb}$ | 921 | 5310 | 3451 |
| $H_{2ha}$ | 2205 | 6231 | 3073 |
| $H_{2hb}$ | 1449 | 6034 | 1874 |
| $H_{3ha}$ | 3066 | 5447 | 1684 |
| $H_{3hb}$ | 3908 | 5936 | 2669 |
| $H_{4ha}$ | 4260 | 4953 | 3725 |
| $H_{4hb}$ | 3874 | 4459 | 2671 |
| $H_{1ia}$ | 3007 | 1289 | −1594 |
| $H_{1ib}$ | 1721 | 1306 | −2615 |
| $H_{2ia}$ | 3703 | 2328 | −2031 |
| $H_{2ib}$ | 2496 | 2303 | −3103 |
| $H_{3ia}$ | 1541 | 3249 | −2509 |
| $H_{3ib}$ | 2638 | 3195 | −1381 |
| $H_{4ia}$ | 101 | 2580 | −2020 |
| $H_{4ib}$ | 1010 | 2761 | −851 |
| $H_{1ja}$ | 4929 | 513 | 470 |
| $H_{1jb}$ | 4341 | −91 | 1129 |
| $H_{2ja}$ | 5823 | −388 | −178 |
| $H_{2jb}$ | 5232 | −992 | 479 |
| $H_{3ja}$ | 3930 | −1396 | −1018 |
| $H_{3jb}$ | 4261 | −668 | −1623 |
| $H_{4ja}$ | 2185 | −862 | −715 |
| $H_{4jb}$ | 2215 | −324 | −1678 |

[a]Hydrogen atoms were included in the structure factor calculations as idealized atoms (assuming $sp^2$— or $sp^3$— hybridization of the carbon atoms and a C—H bond length of 0.96Å) "riding" on their respective carbon atoms. The isotropic thermal parameter of each hydrogen atom was fixed at 1.2 times the equivalent isotropic thermal parameter of the carbon atom to which it is covalently bonded.
[b]Hydrogen atoms are labeled with the same numerical and literal subscripts as their carbon atoms with an additional literal subscript (a, or b) where necessary to distinguish between hydrogen atoms bonded to the same carbon.

TABLE XIV

Bond Lengths Involving Nonhydrogen Atoms in Crystalline
$[Cr(NC_4H_4)_5(OC_4H_8)][Na]_2 \cdot 4(OC_4H_8)^a$

| Type[b] | Length, Å | Type[b] | Length, Å |
|---|---|---|---|
| Cr—$N_{1a}$ | 2.035(6) | $Na_1$—$O_{1g}$ | 2.314(6) |
| Cr—$N_{1b}$ | 2.056(5) | $Na_1$—$O_{1h}$ | 2.271(8) |
| Cr—$N_{1c}$ | 2.044(5) | | |
| Cr—$N_{1d}$ | 2.114(6) | $Na_2$—$O_{1i}$ | 2.365(7) |
| Cr—$N_{1e}$ | 2.024(6) | $Na_2$—$O_{1j}$ | 2.307(7) |
| Cr—$O_{1f}$ | 2.120(5) | $C_{1g}$—$C_{2g}$ | 1.33(2) |
| | | $C_{2g}$—$C_{3g}$ | 1.43(2) |
| $N_{1a}$—$C_{1a}$ | 1.36(1) | $C_{3g}$—$C_{4g}$ | 1.47(2) |
| $N_{1a}$—$C_{4a}$ | 1.38(1) | $C_{1h}$—$C_{2h}$ | 1.51(2) |
| $N_{1b}$—$C_{1b}$ | 1.33(1) | $C_{2h}$—$C_{3h}$ | 1.30(2) |
| $N_{1b}$—$C_{4b}$ | 1.37(1) | $C_{3h}$—$C_{4h}$ | 1.48(2) |
| $N_{1c}$—$C_{1c}$ | 1.41(1) | $C_{1i}$—$C_{2i}$ | 1.41(3) |
| $N_{1c}$—$C_{4c}$ | 1.35(1) | $C_{2i}$—$C_{3i}$ | 1.47(3) |
| $N_{1d}$—$C_{1d}$ | 1.34(1) | $C_{3i}$—$C_{4i}$ | 1.40(3) |
| $N_{1d}$—$C_{4d}$ | 1.36(1) | $C_{1j}$—$C_{2j}$ | 1.44(2) |
| $N_{1e}$—$C_{1e}$ | 1.40(1) | $C_{2j}$—$C_{3j}$ | 1.46(2) |
| $N_{1e}$—$C_{4e}$ | 1.39(1) | $C_{3j}$—$C_{4j}$ | 1.42(2) |
| $O_{1f}$—$C_{1f}$ | 1.42(1) | $O_{1g}$—$C_{1g}$ | 1.38(1) |
| $O_{1f}$—$C_{4f}$ | 1.44(1) | $O_{1g}$—$C_{4g}$ | 1.32(1) |
| | | $O_{1h}$—$C_{1h}$ | 1.38(1) |
| $C_{1a}$—$C_{2a}$ | 1.39(1) | $O_{1h}$—$C_{4h}$ | 1.39(2) |
| $C_{2a}$—$C_{3a}$ | 1.38(1) | $O_{1i}$—$C_{1i}$ | 1.36(2) |
| $C_{3a}$—$C_{4a}$ | 1.37(1) | $O_{1i}$—$C_{4i}$ | 1.40(1) |
| $C_{1b}$—$C_{2b}$ | 1.33(1) | $O_{1j}$—$C_{1j}$ | 1.41(1) |
| $C_{2b}$—$C_{3b}$ | 1.42(1) | $O_{1j}$—$C_{4j}$ | 1.43(1) |
| $C_{3b}$—$C_{4b}$ | 1.31(1) | | |
| $C_{1c}$—$C_{2c}$ | 1.37(1) | $Na_1$—$C_{1a}$ | 2.678(8) |
| $C_{2c}$—$C_{3c}$ | 1.41(1) | $Na_1$—$N_{1d}$ | 2.688(7) |
| $C_{3c}$—$C_{4c}$ | 1.39(1) | $Na_1$—$C_{1d}$ | 2.621(9) |
| $C_{1d}$—$C_{2d}$ | 1.37(1) | | |
| $C_{2d}$—$C_{3d}$ | 1.40(1) | | |
| $C_{3d}$—$C_{4d}$ | 1.34(1) | $Na_2$—$C_{4a}$ | 2.681(7) |
| $C_{1e}$—$C_{2e}$ | 1.37(1) | $Na_2$—$C_{1e}$ | 2.630(9) |
| $C_{2e}$—$C_{3e}$ | 1.43(1) | | |
| $C_{3e}$—$C_{4e}$ | 1.37(1) | | |
| $C_{1f}$—$C_{2f}$ | 1.50(1) | | |
| $C_{2f}$—$C_{3f}$ | 1.43(2) | | |
| $C_{3f}$—$C_{4f}$ | 1.49(2) | | |

[a]The numbers in parentheses are the estimated standard deviations in the last significant digit.
[b]Atoms are labeled in agreement with FIG. 6.

TABLE XV

Bond Angles Involving Nonhydrogen Atoms in Crystalline
$[Cr(NC_4H_4)_5(OC_4H_8)][Na]_2 \cdot 4(OC_4H_8)^a$

| Type[b] | Angle, deg | Type[b] | Angle, deg |
|---|---|---|---|
| $N_{1a}CrN_{1b}$ | 91.2(2) | $O_{1g}Na_1O_{1h}$ | 92.3(3) |
| $N_{1a}CrN_{1c}$ | 91.4(2) | $O_{1g}Na_1C_{1a}$ | 114.3(3) |
| $N_{1a}CrN_{1d}$ | 91.1(2) | $O_{1g}Na_1N_{1d}$ | 139.6(3) |
| $N_{1a}CrN_{1e}$ | 92.8(2) | $O_{1g}Na_1C_{1d}$ | 118.0(3) |
| $N_{1a}CrO_{1f}$ | 178.7(2) | $O_{1h}Na_1C_{1a}$ | 95.6(3) |
| $N_{1b}CrN_{1c}$ | 176.2(2) | $O_{1h}Na_1N_{1d}$ | 127.0(2) |
| $N_{1b}CrN_{1d}$ | 86.7(2) | $O_{1h}Na_1C_{1d}$ | 132.1(3) |
| $N_{1b}CrN_{1e}$ | 93.3(2) | $C_{1a}Na_1N_{1d}$ | 75.1(2) |
| $N_{1b}CrO_{1f}$ | 88.5(2) | $C_{1a}Na_1C_{1d}$ | 103.1(3) |
| $N_{1c}CrN_{1d}$ | 90.4(2) | $N_{1d}Na_1C_{1d}$ | 29.3(2) |
| $N_{1c}CrN_{1e}$ | 89.4(2) | | |
| $N_{1c}CrO_{1f}$ | 88.8(2) | $O_{1i}Na_2O_{1j}$ | 90.7(3) |
| $N_{1d}CrN_{1e}$ | 176.1(2) | $O_{1i}Na_2C_{4a}$ | 109.3(3) |
| $N_{1d}CrO_{1f}$ | 87.6(2) | $O_{1i}Na_2C_{1e}$ | 131.5(2) |
| $N_{1e}CrO_{1f}$ | 88.5(2) | $O_{1j}Na_2C_{4a}$ | 103.2(2) |
| | | $O_{1j}Na_2C_{1e}$ | 115.1(3) |
| $CrN_{1a}C_{1a}$ | 128.7(5) | $C_{4a}Na_2C_{1e}$ | 103.9(3) |
| $CrN_{1a}C_{4a}$ | 126.3(5) | | |
| $CrN_{1b}C_{1b}$ | 127.0(4) | $Na_1O_{1g}C_{1g}$ | 131.4(6) |
| $CrN_{1b}C_{4b}$ | 127.3(5) | $Na_1O_{1g}C_{4g}$ | 124.0(8) |
| $CrN_{1c}C_{1c}$ | 128.5(5) | $Na_1O_{1h}C_{1h}$ | 132.2(7) |
| $CrN_{1c}C_{4c}$ | 126.7(5) | $Na_1O_{1h}C_{4h}$ | 116.6(6) |
| $CrN_{1d}C_{1d}$ | 127.7(5) | $Na_2O_{1i}C_{1i}$ | 120.9(8) |
| $CrN_{1d}C_{4d}$ | 125.7(5) | $Na_2O_{1i}C_{4i}$ | 126.8(7) |
| $CrN_{1e}C_{1e}$ | 127.7(5) | $Na_2O_{1j}C_{1j}$ | 123.1(6) |
| $CrN_{1e}C_{4e}$ | 126.2(4) | $Na_2O_{1j}C_{4j}$ | 125.8(5) |
| $CrO_{1f}C_{1f}$ | 126.4(4) | $C_{1g}O_{1g}C_{4g}$ | 104.3(8) |
| $CrO_{1f}C_{4f}$ | 123.1(5) | $C_{1h}O_{1h}C_{4h}$ | 108.9(9) |
| | | $C_{1}O_{1i}C_{4i}$ | 107.8(11) |
| $C_{1a}N_{1a}C_{4a}$ | 105.0(6) | $C_{1j}O_{1j}C_{4j}$ | 107.7(7) |
| $C_{1b}N_{1b}C_{4b}$ | 105.2(5) | | |
| $C_{1c}N_{1c}C_{4c}$ | 104.0(5) | $O_{1g}C_{1g}C_{2g}$ | 111(1) |
| $C_{1d}N_{1d}C_{4d}$ | 106.6(6) | $C_{1g}C_{2g}C_{3g}$ | 103(1) |
| $C_{1e}N_{1e}C_{4e}$ | 106.0(6) | $C_{2g}C_{3g}C_{4g}$ | 103(1) |
| | | $C_{3g}C_{4g}O_{1g}$ | 110(1) |
| $C_{1f}O_{1f}C_{4f}$ | 110.5(6) | $O_{1h}C_{1h}C_{2h}$ | 106(1) |
| | | $C_{1h}C_{2h}C_{3h}$ | 106(1) |
| $N_{1a}C_{1a}C_{2a}$ | 111.1(7) | $C_{2h}C_{3h}C_{4h}$ | 109(1) |

TABLE XV-continued

Bond Angles Involving Nonhydrogen Atoms in Crystalline [Cr(NC$_4$H$_4$)$_5$(OC$_4$H$_8$)][Na]$_2$—4(OC$_4$H$_8$)[a]

| Type[b] | Angle, deg | Type[b] | Angle, deg |
|---|---|---|---|
| C$_{1a}$C$_{2a}$C$_{3a}$ | 106.1(8) | C$_{3h}$C$_{4h}$O$_{1h}$ | 106(1) |
| C$_{2a}$C$_{3a}$C$_{4a}$ | 107.5(7) | O$_{1i}$C$_{1i}$C$_{2i}$ | 110(2) |
| C$_{3a}$C$_{4a}$N$_{1a}$ | 110.3(7) | C$_{1i}$C$_{2i}$C$_{3i}$ | 105(2) |
| N$_{1b}$C$_{1b}$C$_{2b}$ | 110.6(7) | C$_{2i}$C$_{3i}$C$_{4i}$ | 106(2) |
| C$_{1b}$C$_{2b}$C$_{3b}$ | 107.6(8) | C$_{3i}$C$_{4i}$O$_{1i}$ | 107(1) |
| C$_{2b}$C$_{3b}$C$_{4b}$ | 104.4(7) | O$_{1j}$C$_{1j}$C$_{2j}$ | 106(1) |
| C$_{3b}$C$_{4b}$N$_{1b}$ | 112.2(7) | C$_{1j}$C$_{2j}$C$_{3j}$ | 109(1) |
| N$_{1c}$C$_{1c}$C$_{2c}$ | 112.4(7) | C$_{2j}$C$_{3j}$C$_{4j}$ | 104(1) |
| C$_{1c}$C$_{2c}$C$_{3c}$ | 104.5(7) | C$_{3j}$C$_{4j}$O$_{1j}$ | 108(1) |
| C$_{2c}$C$_{3c}$C$_{4c}$ | 107.8(7) | | |
| C$_{3c}$C$_{4c}$N$_{1c}$ | 111.2(7) | Na$_1$C$_{1a}$N$_{1a}$ | 95.0(4) |
| N$_{1d}$C$_{1d}$C$_{2d}$ | 109.0(7) | Na$_1$C$_{1a}$C$_{2a}$ | 106.7(5) |
| C$_{1d}$C$_{2d}$C$_{3d}$ | 107.6(8) | Na$_1$N$_{1d}$Cr | 107.7(3) |
| C$_{2d}$C$_{3d}$C$_{4d}$ | 105.4(8) | Na$_1$N$_{1d}$C$_{1d}$ | 72.6(4) |
| C$_{3d}$C$_{4d}$N$_{1d}$ | 111.5(7) | Na$_1$N$_{1d}$C$_{4d}$ | 86.4(4) |
| N$_{1e}$C$_{1e}$C$_{2e}$ | 111.0(7) | Na$_1$C$_{1d}$N$_{1d}$ | 78.1(4) |
| C$_{1e}$C$_{2e}$C$_{3e}$ | 105.2(7) | Na$_1$C$_{1d}$C$_{2d}$ | 85.1(6) |
| C$_{2e}$C$_{3e}$C$_{4e}$ | 108.4(8) | | |
| C$_{3e}$C$_{4e}$N$_{1e}$ | 109.5(7) | Na$_2$C$_{4a}$N$_{1a}$ | 90.2(3) |
| | | Na$_2$C$_{4a}$C$_{3a}$ | 104.0(5) |
| O$_{1f}$C$_{1f}$C$_{2f}$ | 104.4(7) | Na$_2$C$_{1e}$N$_{1e}$ | 78.1(4) |
| C$_{1f}$C$_{2f}$C$_{3f}$ | 105.0(9) | Na$_2$C$_{1e}$C$_{2e}$ | 91.7(6) |
| C$_{2f}$C$_{3f}$C$_{4f}$ | 104.9(9) | | |
| C$_{3f}$C$_{4f}$O$_{1f}$ | 104.7(7) | | |

[a]The numbers in parentheses are the estimated standard deviations in the last significant digit.
[b]Atoms are labeled in agreement with FIG. 6.

EXAMPLE VII

The product obtained from the reaction of sodium 2,5-dimethylpyrrolide and CrCl$_2$ used in the preparation of an active catalyst was a light blue solid, Product VI. 2,5-Dimethylpyrrole (5.0 ml/49.1 mmole) was mixed with excess sodium (40% dispersion in mineral spirits) in tetrahydrofuran (125 ml) at ambient temperature. The mixture was refluxed 12 hours under nitrogen then filtered to remove excess sodium. The sodium 2,5-dimethylpyrrolide was used in-site and combined with chromous chloride (3.03 g/24.7 mmole) at ambient temperature. The reaction mixture was refluxed under nitrogen for 48 hours. The gray-green solution was filtered (medium porosity frit) at ambient temperature and stripped of solvent under vacuum, then pumped dry under vacuum for 12 hours resulting in a gray/green solid. This gray/green solid was then washed with pentane resulting in a light blue solid, Product VI, which was collected by filtration. Product VI was used in the preparation of an active catalyst without further purification.

EXAMPLE VIII

Preparation of Catalysts

All polymerization runs were carried out in a two liter reactor under slurry (particle form) conditions. The diluent was isobutane and the reactor temperature was 90° C. Reactor pressure held at 550 psig during the polymerization, with ethylene being fed on demand.

The actual charging of the reactor was accomplished by the following method. After purging the reactor at 100° C. with a stream of nitrogen for at least 15 minutes, the reactor temperature was lowered to 90° C. and a preweighed amount of supported chromium pyrrolide catalyst was charged against a slight countercurrent of nitrogen. One liter of isobutane was then charge to the reactor and finally the reactor pressurized with ethylene.

The ethylene consumed was determined using a precalibrated ethylene flow meter. Samples of the liquid product mixture were taken after 30 minute run time without depressurizing the reactor. This was done by filling to 200–300 psig a steel sampling cylinder adapted to the reactor with a dip tube fitted with a fritted tip extending into the bottom of the reactor vessel. Samples taken this way were analyzed by gas chromatography and gas chromatography-mass spectrometry. Selectivities were normalized to 100%. Solid products were obtained by venting the reactor to atmosphere, separating by decantation of the liquids from the solid material. The solids were then dried at 100° C. in a vacuum oven and weighed. The yield of solid product was obtained by weighing the combined solid and catalyst residues and subtracting from this the preweighed catalyst charge. The yield of volatile products was obtained by subtracting the yield of solid products from the grams of ethylene consumed as recorded by the flow meter.

Activity typically ranged from 300–1500 g product/g catalyst/hour calculated for 30 minute run time, as shown in Table XVI. The product obtained typically was represented by 97–99.5% by weight liquids and 0.5–3% by weight polymer (wax). The liquid fraction was typically 85% hexenes, 11% decenes, 2% tetradecences, based on the total weight of the liquid fraction. The balance of the liquid product mixture was a trace level distribution of olefins typically totaling about 1–2% by weight of the product mixture, see Table XVII.

Active catalysts were prepared from the chromium pyrrolide complexes as follows. All toluene and/or pentane rinses used about 15 to about 30 mls of liquid.

Run 1: 0.158 g of Product V (prepared in THF solvent), which was heated to 80° C. for 4 hours under nitrogen flush to remove residual THF, was slurried with 15 ml toluene at ambient temperature. 9.0 ml of a 1M TEA in hexanes solution was added to the solution and stirred for 24 hours. The formation of a brown solution and the complete dissolution of Product V resulted immediately upon TEA addition. AlPO$_4$(P/Al mole ratio=0.4) (2.00 g) was added to the solution and stirred for an additional 24 hours. The supported catalyst was filtered from the solution as a brown solid, rinsed twice with toluene, and then twice with pentane. 0.3143 g of the catalyst was charged directly to the reactor for polymerization. 1.0 ml of a 0.5% TEA in heptanes solution was charged to the reactor after the catalyst charge but before the isobutane (reactor solvent) charge to purge feedstock poisons.

Run 2: 0.081 g of Product V (prepared in THF solvent), which was heated to 80° C. for 4 hours under nitrogen flush to remove residual THF, was slurried with 15 ml diethylbenzene at ambient temperature. 2.0 ml of a 1M TEA in hexanes solution was added to the solution and stirred for 24 hours. The formation of a brown solution and the complete dissolution of Product V resulted immediately upon TEA addition. AlPO$_4$(P/Al mole ratio=0.4) (1.50 g) was added to the solution and stirred for an additional 1 hour. The supported catalyst was filtered from the solution as a brown solid, rinsed twice with dimethylbenzene, and then twice with pentane. 0.4333 g of the catalyst was charged directly to the reactor for polymerization. 3.0 ml of a 0.5% TEA in heptanes solution was charged to the reactor after the catalyst charge but before the isobutane (reactor solvent) charge to purge feedstock poisons.

Run 3: 0.093 g of Product V (prepared in DME solvent) was slurried with 15 ml toluene at ambient temperature. 5.0 ml of a 1M TEA in hexanes solution was added to the solution and stirred for 24 hours. The formation of a brown solution and the complete dissolution of Product V resulted immediately upon TEA addition. AlPO$_4$(P/Al mole ratio=0.4) (1.0 g) was added to the solution and stirred for an additional 24 hours. The supported catalyst was filtered from the solution as a brown solid, rinsed twice with toluene, and then twice with pentane. 0.1564 g of the catalyst was charged directly to the reactor for polymerization. 3.0 ml of a 0.5% TEA in heptanes solution was charged to the reactor after the catalyst charge but before the isobutane (reactor solvent) charge to purge feedstock poisons.

Run 4: 0.080 g of Product I (prepared in THF solvent) was slurried with 15 ml toluene at ambient temperature. 6.0 ml of a 1M TEA in hexanes solution was added and the solution stirred for 16 hours. The formation of a brown solution and the complete dissolution of Product I resulted immediately upon TEA addition. AlPO$_4$(P/Al mole ratio=0.4) (1.50 g) was added to the solution and stirred for an additional 16 hours. The supported catalyst was filtered from the solution as a brown solid, rinsed twice with toluene, and then twice pentane. 1.1988 g of the catalyst was charged directly to the reactor for polymerization.

Run 5: 0.079 g of Product II (prepared in THF solvent) was slurried with 15 ml toluene at ambient temperature. 2.0 ml of a 1.9M TEA in toluene solution was added to the solution and stirred for 8 hours. The formation of a brown solution and the complete dissolution of Product II resulted immediately upon TEA addition. AlPO$_4$(P/Al mole ratio=0.4) (0.50 g) was added to the solution and stirred for an additional 16 hours. The supported catalyst was filtered from the solution as a brown solid, rinsed twice with toluene, and then twice with pentane. 0.4829 g of the catalyst was charged directly to the reactor for polymerization.

Run 6: 0.071 g of Product V (prepared in THF solvent), which was heated to 80° C. for 4 hours under nitrogen flush to remove residual THF, was slurried with 15 ml toluene at ambient temperature. 2.0 ml of a 1M TEA in hexanes solution was added to the solution and stirred for 1 hour. The formation of a brown solution and the complete dissolution of Product V resulted immediately upon TEA addition. SiO$_2$(2.52 g) was added to the solution and stirred for an additional 2 minutes. The supported catalyst was filtered from the solution as a brown solid, rinsed twice with toluene, and then twice with pentane. All of the catalyst was charged directly to the reactor for polymerization.

Run 7: 0.103 g of Product II (prepared in THF solvent) was slurried with 15 ml toluene at ambient temperature. 1.0 ml of a 1.9M TEA in toluene solution was added to the solution and stirred for 10 minutes. The formation of a brown solution and the complete dissolution of Product II resulted immediately upon TEA addition. Al$_2$O$_3$ (2.27 g) was added to the solution and stirred for an additional 2 minutes. The supported catalyst was filtered from the solution as a brown solid, rinsed twice with toluene, and then twice with pentane. 1.2926 g of the catalyst was charged directly to the reactor for polymerization.

Run 8: 0.120 g of Product I (prepared in THF solvent) was slurried with 15 ml toluene at ambient temperature. 2.0 ml of a 1M TEA in hexanes solution was added to the solution and stirred for 2 days. The formation of a brown solution and the complete dissolution of Product I resulted immediately upon TEA addition. SiO$_2$(1.0 g) was added to the solution and stirred for an additional 3 weeks. The supported catalyst was filtered from the solution as a brown solid, rinsed twice with toluene, and then twice with pentane. All of the catalyst was charged directly to the reactor for polymerization.

Run 9: 0.106 g of Product III (prepared in THF solvent) was slurried with 15 ml toluene at ambient temperature. 2.5 ml of a 1.9M TEA in toluene solution was added to the solution and stirred for 2 hours. The formation of a brown solution and the complete dissolution of Product III resulted immediately upon TEA addition. AlPO$_4$(P/Al mole ratio=0.4) (0.65 g) was added to the solution and stirred for an additional 2 hours. The supported catalyst was filtered from the solution as a brown solid, rinsed twice with toluene, and then twice with pentane. All of the catalyst was charged directly to the reactor for polymerization. 1.5 ml of a 1.0% TEA in pentane solution was charged to the reactor after the catalyst charge but before the isobutane (reactor solvent) charge to purge feedstock poisons.

Run 10: 0.030 g of Product V (prepared in THF solvent) which was heated to 80° C. for 4 hours under nitrogen flush to remove residual THF was slurried with 15 ml toluene at ambient temperature. 3.0 ml of a 1M TEA in hexanes solution was added to the solution and stirred for 16 hours. The formation of a brown solution and the complete dissolution of Product V resulted immediately upon TEA addition. AlPO$_4$(P/Al=0.9) (2.0 g) was added to the solution and stirred for an additional 16 hours. The supported catalyst was filtered from the solution as a brown solid, rinsed twice with toluene, and then twice with pentane. 0.322/g of catalyst was charged directly to the reactor for polymerization.

Run 11: 0.067 g of Product V (prepared in THF solvent) was slurried with 15 ml pentane at ambient temperature. 4.0 ml of a 1M TEA in hexanes solution was added to the solution and stirred for 24 hours. The formation of a brown solution and the complete dissolution of Product V resulted immediately upon TEA addition. AlPO$_4$(P/Al mole ratio=0.4) (1.0 g) was added to the solution and stirred for an additional 24 hours. The supported catalyst was filtered from the solution as a brown solid, rinsed twice with pentane. All of the catalyst was charged directly to the reactor for polymerization. 3.0 ml of a 0.5% TEA in heptanes solution was charged to the reactor after the catalyst charge but before the isobutane (reactor solvent) charge to purge feedstock poisons.

Run 12: 0.073 g of Product V (prepared in THF solvent), which was heated to 80° C. for 4 hours under nitrogen flush to remove residual THF, was slurried with 15 ml toluene at ambient temperature. 6.0 ml of a 1M TEA in hexanes solution was added and the solution stirred for 24 hours. The formation of a brown solution and the complete dissolution of Product V resulted immediately upon TEA addition. P/SiO$_2$ (7.0 g) was added to the solution and stirred for an additional 24 hours which nearly decolorized it. The supported catalyst was filtered from the solution as a brown solid, rinsed twice with toluene, and then twice with pentane. 2.85 g of catalyst was charged directly to the reactor for polymerization.

Run 13: 0.125 g or Product II was slurried with 15 ml diethylbenzene at ambient temperature. 9.0 ml of a 1M TEA in hexane solution was added to the solution and stirred for 8 hours. The formation of a brown solution and the complete dissolution of Product II resulted immediately upon TEA addition. F/Al$_2$O$_3$ (2.0 g) was added to the solution and stirred for an additional 12 hours. The supported catalyst was filtered from the solution as a brown solid, rinsed twice with toluene, and then twice with pentane. 0.5477 g of catalyst was charged directly to the reactor for polymerization.

Run 14: 0.125 g of Product VI was slurried with 15 ml toluene at ambient temperature. 1.5 ml of a 1M TEA in hexanes solution was added and the solution stirred for 10 minutes. The formation of a red/brown solution and the complete dissolution of Product VI resulted immediately upon TEA addition. SiO$_2$ (2.0 g) was added to the solution and stirred for an additional 1 minute which nearly decolorized it. The supported silica catalyst was filtered from the solution as a red/brown solid, rinsed twice with toluene, and then twice with pentane. All of the catalyst was charged directly to the reactor for polymerization.

Run 15: 0.30 g of Product V (prepared in DME solvent) was dissolved with 15 ml of dimethoxyethane forming a green solution. This solution was then mixed with 0.6 g of AlPO$_4$(P/Al$_4$ mole ratio=0.4) (2.00 g) and the mixture was stirred 1 hour. The green supported material was filtered from the solution, rinsed with dimethoxyethane and dried with a nitrogen purge at 90° C. This material was then stirred with 15 ml of toluene and 3 ml of triethylaluminum (Aldrich 1.0M, hexanes) for an additional 3 hours. The brown supported catalyst was collected by filtration, rinsed with pentane, and dried under vacuum. 0.4609 g of the catalyst was charged directly to the reactor for polymerization. 3.0 ml of a 0.5% TEA in heptanes solution was charged to the reactor after the catalyst charge but before the isobutane (reactor solvent) charge to purge feedstock poisons.

Run 16: 0.058 g of Product V (prepared in THF solvent) which was heated to 80° C. for 4 hours under nitrogen flush to remove residual THF was slurried with 15 ml benzene at ambient temperature. 4.0 ml of a 1M TEA in hexanes solution was added and the solution stirred for 2 hours. The formation of a brown solution and the complete dissolution of Product V resulted immediately upon TEA addition. AlPO$_4$(P/Al mole ratio=0.4) (1.0 g) was added to the solution and stirred for 1 hour. The supported catalyst was filtered from the solution as a brown solid, rinsed twice with benzene, and then twice with pentane. All of the catalyst was charged directly to the reactor for polymerization. 3.0 ml of a 0.5% TEA in heptanes solution was charged to the reactor after the catalyst charge but before the isobutane (reactor solvent) charge to purge feedstock poisons.

Run 17: 0.1610 g of Product I was charged directly to the reactor at 90° C. The reactor was charged with 1 liter isobutane and pressurized to 550 psig with ethylene. No ethylene consumption was detected, therefore 50 psig of dihydrogen was charged to the reactor which did not initiate ethylene consumption. Ethylene consumption was initiated after 2.0 ml of 1M TEA in hexane solution was charged.

Run 18: 0.3528 g of Product VI was charged directly to the reactor at 90° C. The reactor was charged with 1 liter isobutane and pressurized to 550 psig with ethylene. No ethylene consumption was detected, therefore 2.0 ml of a 1M TEA in hexanes solution was charged which did initiate ethylene consumption.

Run 19: 0.3482 g of Product VI was charged directly to the reactor at 90° C. The reactor was also charged with 2.0 ml of a 1M TEA in hexanes solution prior to a 1 liter isobutane charge. The reactor was then pressurized to 550 psig with ethylene. No ethylene consumption was detected, therefore 30 psi of dihydrogen was charged to the reactor which initiated ethylene consumption.

Run 20: 0.202 g of Product V (prepared in dimethoxyethane (DME) solvent), 6.0 ml of a 1.9M TEA in toluene solution, and 2.0 g of AlPO$_4$ (P/Al mole ratio=0.4) were mixed with 15 ml toluene at ambient temperature. The formation of a brown solution and the complete dissolution of Product V resulted immediately upon mixing. The brown solution was stirred for 48 hours. The supported catalyst was filtered from the solution as a brown solid, rinsed twice with toluene, and then twice with pentane. 0.0671 g of the catalyst was charged directly to the reactor for polymerization. 1.0 ml of a 0.5% TEA in heptanes solution was charged to the reactor after the catalyst charge but before the isobutane (reactor solvent) charge to purge feedstock poisons.

The data in Table XVI show that the inventive chromium compounds can be used either supported (Runs 1-16, 20) or unsupported (Runs 17-19) to polymerize and/or trimerize olefins. Furthermore, conditions can be varied to increase the amount of trimer product (Runs 1-5 and 9) or to have a higher yield of solid, or polymer, product (Runs 6, 7, and 13). Runs 1, 3, and 20 demonstrate that high activities are attainable.

TABLE XVI

| Run[a] | Catalyst | Support[b] | Products | Activity[c] |
| --- | --- | --- | --- | --- |
| 1 | (V)/TEA/Toluene | AlPO$_4$ | 98.4% liquids, 1.6% solids | 1030 |
| 2 | (V)/TEA/Diethylbenzene | AlPO$_4$ | 99.4% liquids, 0.6% solids | 730 |
| 3 | (V)/TEA/Toluene | AlPO$_4$ | 99.4% liquids, 0.6% solids | 1450 |
| 4 | (I)/TEA/Toluene | AlPO$_4$ | 98.6% liquids, 1.4% solids | 360[d] |
| 5 | (II)/TEA/Toluene | AlPO$_4$ | 98.2% liquids, 1.8% solids | 580 |
| 6 | (V)/TEA/Toluene | SiO$_2$ | 89.0% liquids, 11.0% solids | 80 |
| 7 | (II)/TEA/Toluene | Al$_2$O$_3$ | 55.8% liquids, 44.2% solids | 50 |
| 8 | (I)/TEA/Toluene | SiO$_2$ | 93.3% liquids, 6.7% solids | 400 |
| 9 | (III)/TEA/Toluene | AlPO$_4$ | 99.8% liquids, 0.2% solids | 100 |
| 10 | (V)/TEA/Toluene | AlPO$_4$(.9) | 96.8% liquids, 3.2% solids | 930 |
| 11 | (V)/TEA/Toluene | AlPO$_4$ | (trace) liquids, (trace) solids | unreactive |
| 12 | (V)/TEA/Toluene | P/SiO$_2$ | 98.1% liquids, 1.9% solids | 90 |
| 13 | (II)/TEA/Diethylbenzene | F/Al$_2$O$_3$ | 88.0% liquids, 12.0% solids | 300 |
| 14 | (VI)/TEA/Toluene | SiO$_2$ | 94.3% liquids, 5.7% solids | 40 |
| 15 | (V)/DME | AlPO$_4$ | 98.0% liquids, 2.0% solids | 550 |
| 16 | (V)/TEA/Benzene | AlPO$_4$ | 99.1% liquids, 0.9% solids | 500 |
| 17 | (I)/TEA | unsupported | 98.3% liquids, 1.7% solids | 340 |
| 18 | (VI)/TEA | unsupported | 99.4% liquids, 0.6% solids | 180 |
| 19 | (VI)/TEA | unsupported | 98.1% liquids, 1.9% solids | 230 |

TABLE XVI-continued

| Run[a] | Catalyst | Support[b] | Products | Activity[c] |
|---|---|---|---|---|
| 20 | (V)/TEA | AlPO$_4$ | 99.5% liquids, 0.5% solids | 2760 |

[a]All runs were made at 90° C., isobutane solvent, 550 psi total pressure.
[b]P/Al mole ratio = 0.4; except Run 10 whereby P/Al mole ratio = 0.9.
[c]Grams product/grams catalyst/hour based on 30 min. run times.
[d]Believed to to be lower than actual due to experimental error; actual value believe to be near 2000.

TABLE XVII

| Run | C4 | 1-hexene | C6 | C8 | C10 | C12 | C14 | C16–C28 |
|---|---|---|---|---|---|---|---|---|
| 1 | 0.05 | 81.92 | 7.76 | 0.49 | 9.12 | 0.09 | 0.52 | .05 |
| 2 | 0.10 | 78.80 | 7.49 | 0.58 | 11.36 | 0.10 | 1.01 | .56 |
| 3 | 0.06 | 82.19 | 7.68 | 0.45 | 8.85 | 0.08 | 0.58 | .11 |
| 5 | 0.10 | 83.40 | 7.08 | 0.62 | 8.08 | 0.05 | 0.42 | .25 |
| 6 | 0.55 | 78.70 | 5.52 | 1.84 | 11.24 | 0.42 | 1.26 | .47 |
| 16 | 0.06 | 72.85 | 13.61 | 0.31 | 12.06 | 0.09 | 0.93 | .09 |
| 19 | 6.03 | 71.66 | 6.09 | 3.61 | 9.42 | 1.17 | 1.41 | .61 |

EXAMPLE IX

Figure 7:
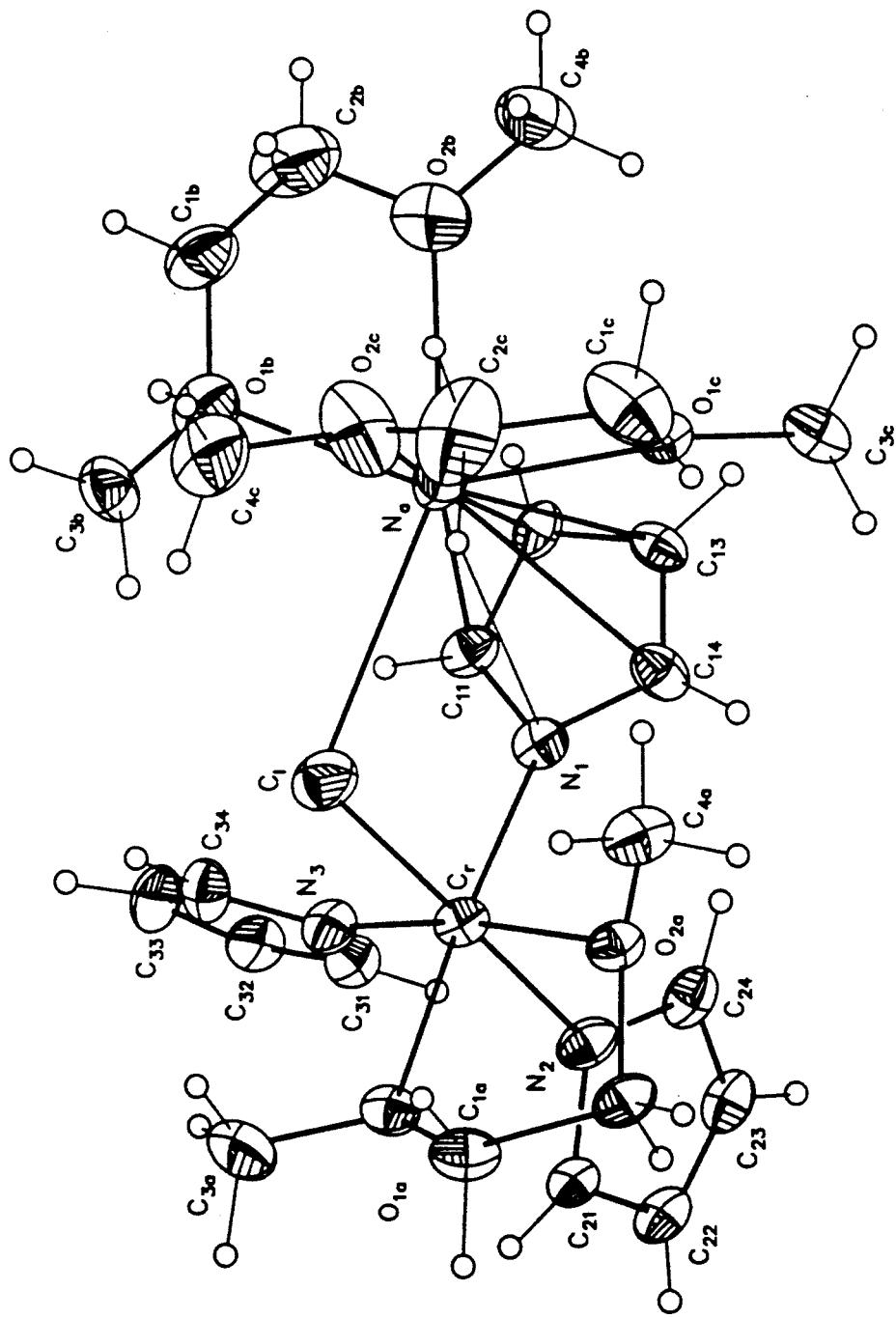
FIG. 7 is a computer generated ORTEP drawing of a molecule of Product V, $Cr(NC_4H_4)_3Cl(O_2C_2H_4(CH_3)_2)_3Na$, which includes the entire crystal structure or lattice, as determined by single crystal x-ray crystallography.
Figure 8:
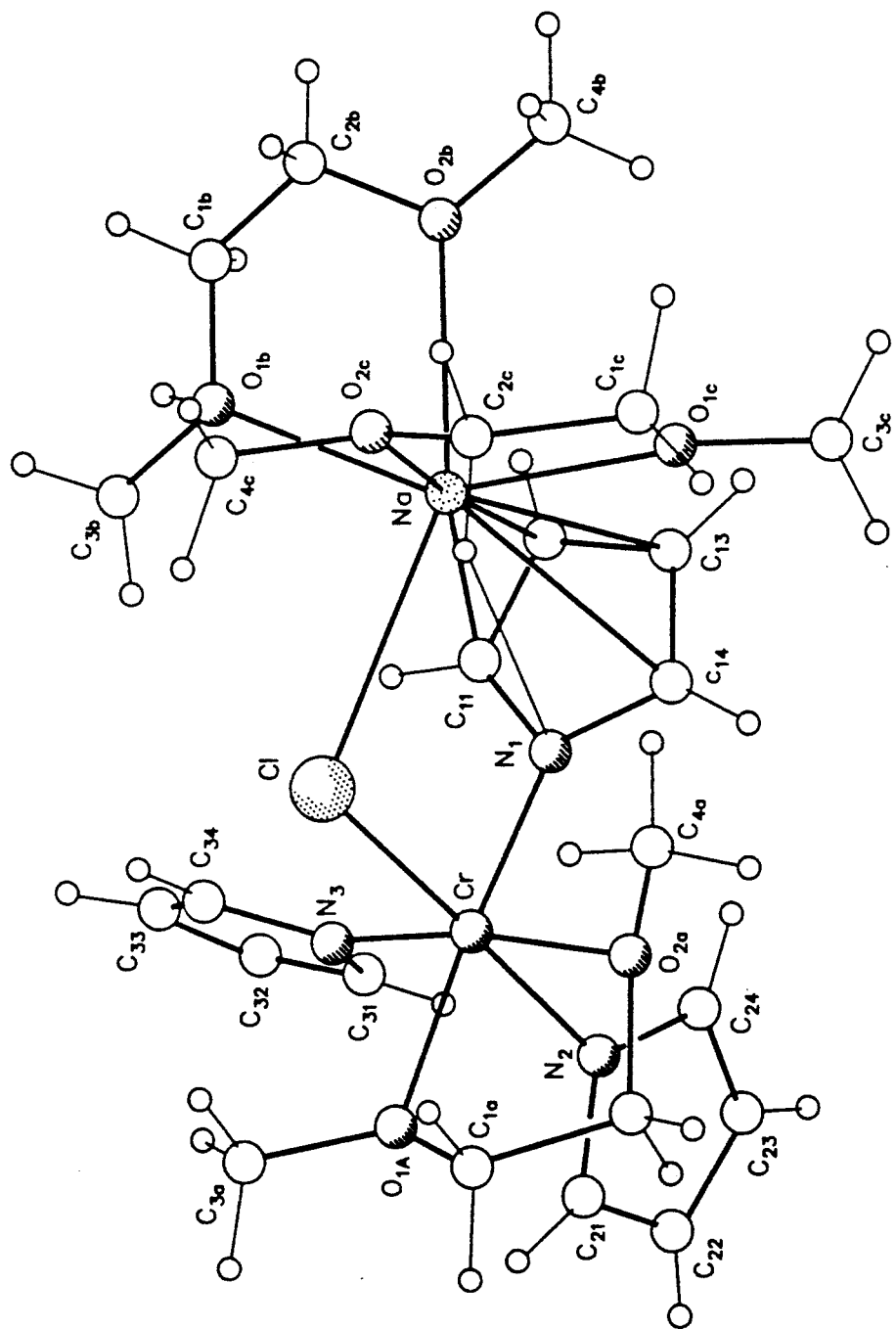
FIG. 8 is a further simplified ball and stick projection of same molecule shown in FIG. 7.
Figure 9:
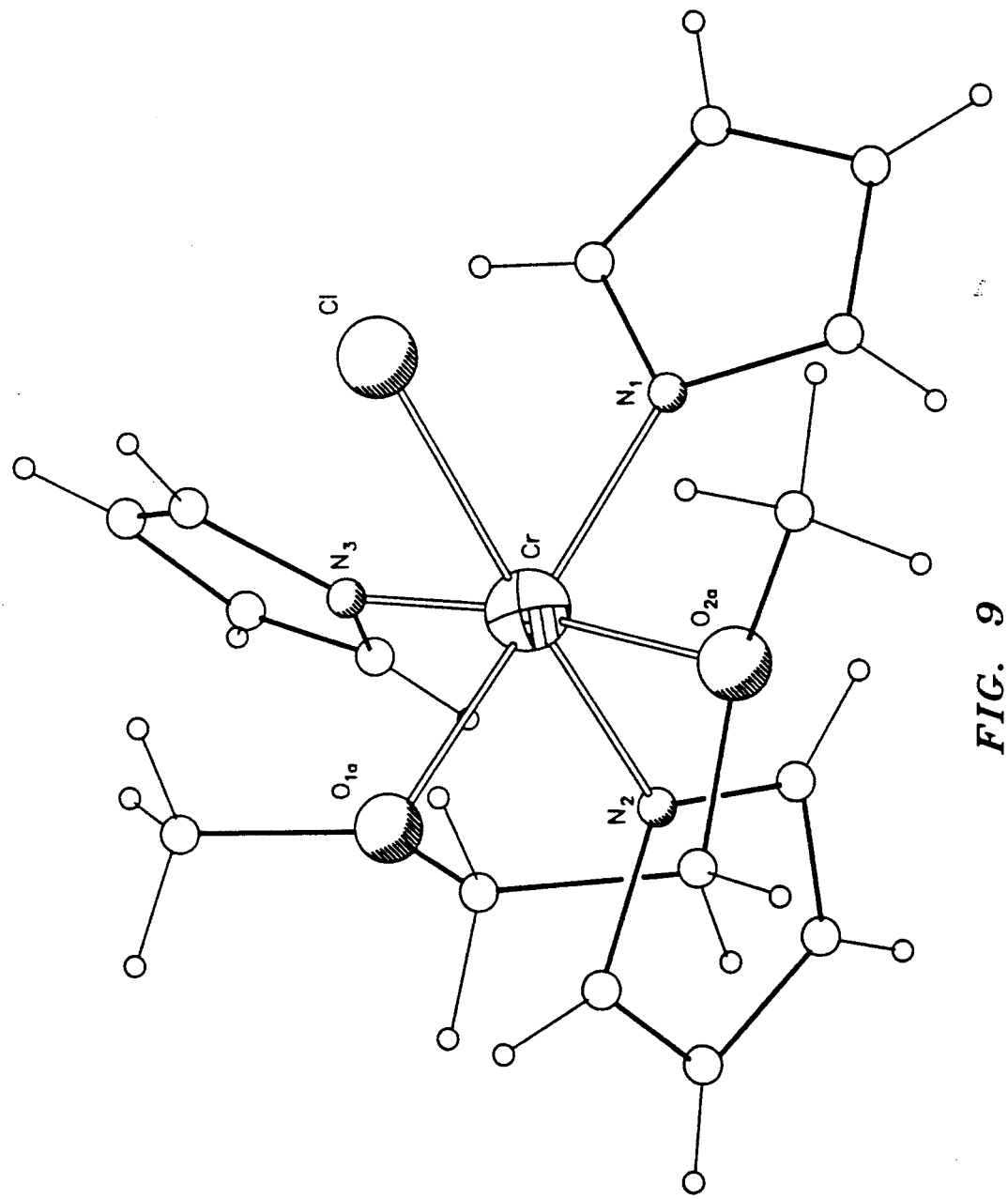
FIG. 9 is a further simplified ball and stick projection of $[Cr(NC_4H_4)_3Cl(O_2C_2H_4(CH_3)_2)]^{-1}$, with the exception of the chromium atom which is represented as a thermal ellipsoid. This is the same molecule as that shown in FIGS. 7 and 8, however, the entire crystal structure, or lattice, is not shown in FIG. 9.

Single crystal x-ray structures were obtained for Cr(NC$_4$H$_4$)$_3$Cl(O$_2$C$_2$H$_4$(CH$_3$)$_2$)$_3$Na, shown in FIGS. 7 and 8, and Cr(NC$_4$H$_4$)$_3$Cl(O$_2$C$_2$H$_4$(CH$_3$)$_2$), and shown in FIG. 9. These crystals were obtained in accordance with the procedure given in Example III. However, x-ray quality crystals were obtained after the dark green, filtered solution was maintained at ambient temperature and pressure under an inert atmosphere, nitrogen, for a time of about 2 days. Analysis calculated for C$_{24}$H$_{42}$N$_3$O$_6$CrNaCl: C, 49-78; H, 7.31; N, 7.26% by weight. Found: C, 49.80; H 7.39; N, 7.18% by weight.

The description of the single-crystal sample and mounting used for data collection are as follows:
Color: Green/black
Shape: Rectangular parallelepiped
Dimensions: 0.44×0.62×0.62 mm
Crystal Mount: Crystal was glued to the inside of a thin-walled glass capillary and sealed under N$_2$.
Crystal Orientation: Crystal was oriented with its longer edges nearly parallel to the phi axis of the diffractometer.
Width at Half-height from ω Scans: 0.38°
The space group and cell data are as follows:
Crystal System: Monoclinic
Space Group and Number:[2] P2$_1$/c-C$_{2h}^5$ (No. 14)
Number of Computer-Centered Reflections Used in the Least-Squares
Refinement of the Cell Dimensions: 15 20°>25°, °C.=20±1
Lattice Constants with esd's:

| a = 8.135(2)Å | α = 90.00° | V = 3027(1)Å$^3$ |
|---|---|---|
| b = 22.337(5)Å | β = 91.67(2)° | Z = 4 |
| c = 16.667(4)Å | δ = 90.00° | λ = 0.71073Å |

Molecular Weight: 579.05 amu
Calculated Density: 1.271 g/cn$^{-3}$
Linear Absorption Coefficient:[3a] 0.51 mm$^{-1}$
Tables XVIII–XXII list the resultant parameters used to generate the molecular structures shown in FIGS. 7 and 8.

TABLE XVIII

Atomic Coordinates for Nonhydrogen Atoms in Crystalline [Cr(NC$_4$H$_4$)$_3$(Cl)(O$_2$C$_2$H$_4$(CH$_3$)$_2$)$_3$Na][a]

| Atom Type[b] | Fractional Coordinates | | | Equivalent Isotropic Thermal Parameter, B, Å$^2$ × 10[c] |
|---|---|---|---|---|
| | 10$^4$x | 10$^4$y | 10$^4$z | |
| Cr | −1030(1) | 559(1) | 3005(1) | 30(1) |
| Cl | 135(1) | −26(1) | 1981(1) | 41(1) |
| Na | −2167(2) | −1011(2) | 1832(1) | 46(1) |
| N$_1$ | −3062(4) | 65(2) | 2907(2) | 35(1) |
| C$_{11}$ | −4107(5) | 63(2) | 2251(3) | 40(1) |
| C$_{12}$ | −5189(5) | −409(2) | 2291(3) | 51(1) |
| C$_{13}$ | −4810(5) | −713(2) | 2998(3) | 51(1) |
| C$_{14}$ | −3512(5) | −414(2) | 3361(3) | 46(1) |
| N$_2$ | −1817(4) | 1027(2) | 3950(2) | 37(1) |
| C$_{21}$ | −1188(6) | 1558(2) | 4234(3) | 47(1) |
| C$_{22}$ | −2205(7) | 1790(2) | 4799(3) | 60(2) |
| C$_{23}$ | −3499(7) | 1398(2) | 4874(3) | 60(2) |
| C$_{24}$ | −3248(5) | 934(2) | 4349(2) | 43(1) |
| N$_3$ | −1892(4) | 1185(2) | 2260(2) | 35(1) |
| C$_{31}$ | −3100(5) | 1588(2) | 2434(3) | 41(1) |
| C$_{32}$ | −3573(6) | 1901(2) | 1757(3) | 53(1) |
| C$_{33}$ | −2631(6) | 1686(2) | 1130(3) | 51(1) |
| C$_{34}$ | −1620(6) | 1249(2) | 1453(3) | 46(1) |
| O$_{1a}$ | 1317(3) | 971(1) | 3154(2) | 40(1) |
| O$_{2a}$ | 153(3) | −12(1) | 3878(2) | 40(1) |
| C$_{1a}$ | 2459(5) | 631(2) | 3651(3) | 53(1) |
| C$_{2a}$ | 1443(6) | 329(2) | 4268(3) | 53(1) |
| C$_{3a}$ | 2156(6) | 1247(2) | 2495(3) | 58(2) |
| C$_{4a}$ | 653(6) | −625(2) | 3733(3) | 49(1) |
| O$_{1b}$ | −2558(4) | −783(2) | 398(2) | 62(1) |
| O$_{2b}$ | −3877(5) | −1772(2) | 1111(2) | 76(1) |
| C$_{1b}$ | −3618(9) | −1166(3) | −25(4) | 89(2) |
| C$_{2b}$ | −3627(9) | −1765(3) | 302(4) | 83(2) |
| C$_{3b}$ | −2410(8) | −207(3) | 61(4) | 79(2) |
| C$_{4b}$ | −4149(9) | −2328(3) | 1440(5) | 106(3) |
| O$_{1c}$ | −1334(4) | −1823(2) | 2911(2) | 65(1) |
| O$_{2c}$ | 235(5) | −1589(2) | 1529(3) | 87(2) |
| C$_{1c}$ | 71(7) | −2144(3) | 2724(4) | 83(2) |
| C$_{2c}$ | 951(8) | −1913(4) | 2067(4) | 107(3) |
| C$_{3c}$ | −2090(8) | −2017(3) | 3614(4) | 83(2) |
| C$_{4c}$ | 1224(8) | −1393(3) | 900(4) | 88(2) |

[a]The numbers in parentheses are the estimated standard deviations in the last significant digit.
[b]Atoms are labeled in agreement with FIG. 7.
[c]This is one-third of the trace of the orthogonalized B$_{ij}$ tensor.

TABLE XIX

Anisotropic Thermal Parameters for Nonhydrogen Atoms in Crystalline [Cr(NC$_4$H$_4$)$_3$(Cl)(O$_2$C$_2$H$_4$(CH$_3$)$_2$)$_3$Na][a,b]

| Atom Type[c] | Anisotropic Thermal Parameter (Å$^2$ × 10) | | | | | |
|---|---|---|---|---|---|---|
| | B$_{11}$ | B$_{22}$ | B$_{33}$ | B$_{12}$ | B$_{13}$ | B$_{23}$ |
| Cr | 28(1) | 31(1) | 30(1) | 2(1) | −0(1) | −2(1) |
| Cl | 39(1) | 43(1) | 41(1) | 2(1) | 5(1) | −9(1) |
| Na | 47(1) | 48(1) | 44(1) | 0(1) | 3(1) | −4(1) |
| N$_1$ | 31(1) | 39(2) | 35(2) | 0(1) | 2(1) | −3(1) |
| C$_{11}$ | 31(2) | 47(2) | 41(2) | 0(2) | −1(2) | −7(2) |
| C$_{12}$ | 33(2) | 59(3) | 61(3) | −3(2) | −4(2) | −16(2) |
| C$_{13}$ | 35(2) | 39(2) | 79(3) | −6(2) | 8(2) | 3(2) |
| C$_{14}$ | 39(2) | 45(2) | 54(2) | 1(2) | 2(2) | 10(2) |
| N$_2$ | 36(2) | 38(2) | 36(2) | 7(1) | −3(1) | −8(1) |
| C$_{21}$ | 55(2) | 38(2) | 47(2) | 9(2) | −6(2) | −5(2) |
| C$_{22}$ | 88(3) | 46(3) | 44(2) | 32(2) | −9(2) | −12(2) |
| C$_{23}$ | 65(2) | 74(3) | 42(2) | 32(2) | 7(2) | 0(2) |
| C$_{24}$ | 37(2) | 55(2) | 37(2) | 14(2) | −0(2) | 1(2) |
| N$_3$ | 38(2) | 35(2) | 32(2) | 3(1) | 0(1) | −0(1) |
| C$_{31}$ | 35(2) | 43(2) | 43(2) | 6(2) | −3(2) | 1(2) |
| C$_{32}$ | 52(2) | 47(2) | 58(3) | 8(2) | −11(2) | 6(2) |
| C$_{33}$ | 62(3) | 51(3) | 39(2) | −2(2) | −8(2) | 12(2) |
| C$_{34}$ | 52(2) | 45(2) | 40(2) | −1(2) | 2(2) | 2(2) |

TABLE XIX-continued

Anisotropic Thermal Parameters for Nonhydrogen Atoms in Crystalline $[Cr(NC_4H_4)_3(Cl)(O_2C_2H_4(CH_3)_2)_3Na]^{a,b}$

| Atom Type[c] | Anisotropic Thermal Parameter ($Å^2 \times 10$) | | | | | |
|---|---|---|---|---|---|---|
| | $B_{11}$ | $B_{22}$ | $B_{33}$ | $B_{12}$ | $B_{13}$ | $B_{23}$ |
| $O_{1a}$ | 32(1) | 40(1) | 50(2) | −1(1) | −3(1) | −5(1) |
| $O_{2a}$ | 40(1) | 38(1) | 41(1) | 6(1) | −7(1) | −1(1) |
| $C_{1a}$ | 33(2) | 50(3) | 73(3) | 4(2) | −13(2) | −10(2) |
| $C_{2a}$ | 53(2) | 55(3) | 51(2) | 10(2) | −24(2) | −10(2) |
| $C_{3a}$ | 45(2) | 53(3) | 76(3) | −15(2) | 8(2) | −5(3) |
| $C_{4a}$ | 50(2) | 40(2) | 58(3) | 12(2) | −8(2) | −1(2) |
| $O_{1b}$ | 76(2) | 63(2) | 47(2) | −14(2) | −5(2) | 1(2) |
| $O_{2b}$ | 101(3) | 62(2) | 63(2) | −28(2) | −5(2) | −2(2) |
| $C_{1b}$ | 120(5) | 91(4) | 56(3) | −29(4) | −25(3) | −3(3) |
| $C_{2b}$ | 116(5) | 64(3) | 68(4) | −18(3) | −24(3) | −12(3) |
| $C_{3b}$ | 81(4) | 84(4) | 72(4) | −9(3) | −1(3) | 19(3) |
| $C_{4b}$ | 118(5) | 84(4) | 113(5) | −51(4) | −38(4) | 29(4) |
| $O_{1c}$ | 61(2) | 64(2) | 70(2) | 8(2) | 0(2) | 4(2) |
| $O_{2c}$ | 74(2) | 76(3) | 112(3) | 29(2) | 31(2) | 30(2) |
| $C_{1c}$ | 73(3) | 65(3) | 113(5) | 23(3) | 9(3) | 25(3) |
| $C_{2c}$ | 83(4) | 143(6) | 96(5) | 61(4) | 24(4) | 14(5) |
| $C_{3c}$ | 84(4) | 64(3) | 101(5) | −8(3) | 3(4) | 16(3) |
| $C_{4c}$ | 77(4) | 98(5) | 90(5) | 13(3) | 29(3) | −5(4) |

[a]The numbers in parentheses are the estimated standard deviations in the last significant digit.
[b]The form of the anisotropic thermal parameter is given in reference 8 on page 6 of the crystal structure analysis report.
[c]Atoms are labeled in agreement with FIG. 7.

TABLE XX

Atomic Coordinates for Hydrogen Atoms in Crystalline $[Cr(NC_4H_4)_3(Cl)(O_2C_2H_4(CH_3)_2)_3Na]^a$

| Atom Type[b] | Fractional Coordinates | | |
|---|---|---|---|
| | $10^4x$ | $10^4y$ | $10^4z$ |
| $H_{11}$ | −4089 | 350 | 1823 |
| $H_{12}$ | −6043 | −509 | 1905 |
| $H_{13}$ | −5349 | −1064 | 3195 |
| $H_{14}$ | −2993 | −526 | 3863 |
| $H_{21}$ | −188 | 1740 | 4063 |
| $H_{22}$ | −2044 | 2158 | 5089 |
| $H_{23}$ | −4404 | 1441 | 5226 |
| $H_{24}$ | −3967 | 597 | 4273 |
| $H_{31}$ | −3554 | 1644 | 2954 |
| $H_{32}$ | −4392 | 2210 | 1720 |
| $H_{33}$ | −2680 | 1817 | 581 |
| $H_{34}$ | −840 | 1021 | 1159 |
| $H_{1aa}$ | 3014 | 339 | 3336 |
| $H_{1ab}$ | 3254 | 892 | 3906 |
| $H_{2aa}$ | 967 | 626 | 4606 |
| $H_{2ab}$ | 2127 | 67 | 4588 |
| $H_{3aa}$ | 1391 | 1487 | 2185 |
| $H_{3ab}$ | 2589 | 938 | 2162 |
| $H_{3ac}$ | 3040 | 1495 | 2696 |
| $H_{4aa}$ | −256 | −834 | 3484 |
| $H_{4ab}$ | 926 | −806 | 4242 |
| $H_{4ac}$ | 1586 | −646 | 3395 |
| $H_{1ba}$ | −4712 | −1006 | −11 |
| $H_{1bb}$ | −3277 | −1186 | −570 |
| $H_{2ba}$ | −2588 | −1951 | 204 |
| $H_{2bb}$ | −4492 | −1988 | 37 |
| $H_{3ba}$ | −1696 | 26 | 407 |
| $H_{3bb}$ | −3461 | −14 | 7 |
| $H_{3bc}$ | −1935 | −243 | −458 |
| $H_{4ba}$ | −4380 | −2289 | 2000 |
| $H_{4bb}$ | −3108 | −2524 | 1385 |
| $H_{4bc}$ | −4998 | −2561 | 1178 |
| $H_{1ca}$ | 795 | −2146 | 3189 |
| $H_{1cb}$ | −255 | −2547 | 2596 |
| $H_{2ca}$ | 1398 | −2252 | 1795 |
| $H_{2cb}$ | 1831 | −1676 | 2294 |
| $H_{3ca}$ | −3168 | −1848 | 3661 |
| $H_{3cb}$ | −1397 | −1884 | 4055 |
| $H_{3cc}$ | −2164 | −2446 | 3624 |
| $H_{4ca}$ | 456 | −1357 | 454 |
| $H_{4cb}$ | 2033 | −1690 | 780 |
| $H_{4cc}$ | 1756 | −1015 | 996 |

[a]The 6 methyl groups were refined as rigid rotors with $sp^3$-hybridized geometry and C—H bond lengths of 0.96Å. The initial orientation of each methyl group was determined from difference Fourier positions for the hydrogen atoms. The final orientation of each methyl group was determined by three rotational parameters. The refined positions for the rigid rotor methyl groups gave O—C—H angles which ranged from 103° to 115°. The remaining hydrogen atoms were included in the structure factor calculations as idealized atoms (assuming $sp^2$- or $sp^3$-hybridization of the carbon atoms and a C—H bond length of 0.96Å) "riding" on their respective carbon atoms. The isotropic thermal parameter of each hydrogen was fixed at 1.2 times the equivalent isotropic thermal parameter of the carbon atom to which it is covalently bonded.
[b]Hydrogens are labeled with the same subscripts as their carbon atoms with an additional literal subscript (a, b or c) where necessary to distinguish between hydrogen atoms bonded to the same carbon.

TABLE XXI

Bond Lengths Involving Nonhydrogen Atoms in Crystalline $[Cr(NC_4H_4)_3(Cl)(O_2C_2H_4(CH_3)_2)_3Na]^a$

| Type[b] | Length, Å | Type[b] | Length, Å |
|---|---|---|---|
| Cr-Cl | 2.369(1) | Cr-$N_1$ | 1.990(3) |
| | | Cr-$N_2$ | 2.010(3) |
| Cr-$O_{1a}$ | 2.128(3) | Cr-$N_3$ | 1.986(3) |
| Cr-$O_{2a}$ | 2.142(3) | | |
| $N_1$-$C_{11}$ | 1.365(5) | $C_{11}$-$C_{12}$ | 1.376(6) |
| $N_1$-$C_{14}$ | 1.366(6) | $C_{12}$-$C_{13}$ | 1.386(7) |
| $N_2$-$C_{21}$ | 1.370(6) | $C_{13}$-$C_{14}$ | 1.376(6) |
| $N_2$-$C_{24}$ | 1.374(5) | $C_{21}$-$C_{24}$ | 1.373(7) |
| $N_3$-$C_{31}$ | 1.370(5) | $C_{22}$-$C_{23}$ | 1.377(8) |
| $N_3$-$C_{34}$ | 1.376(6) | $C_{23}$-$C_{24}$ | 1.375(7) |
| | | $C_{31}$-$C_{32}$ | 1.373(7) |
| $O_{1a}$-$C_{1a}$ | 1.443(5) | $C_{32}$-$C_{33}$ | 1.399(7) |
| $O_{1a}$-$C_{3a}$ | 1.448(6) | $C_{33}$-$C_{34}$ | 1.375(7) |
| $O_{2a}$-$C_{2a}$ | 1.437(5) | | |
| $O_{2a}$-$C_{4a}$ | 1.450(5) | $C_{1a}$-$C_{2a}$ | 1.498(7) |
| $O_{1b}$-$C_{1b}$ | 1.391(8) | $C_{1b}$-$C_{2b}$ | 1.445(9) |
| $O_{1b}$-$C_{3b}$ | 1.410(7) | $C_{1c}$-$C_{2c}$ | 1.422(10) |
| $O_{2b}$-$C_{2b}$ | 1.370(7) | | |
| $O_{2b}$-$C_{4b}$ | 1.379(8) | Na ... Cr | 4.108(2) |
| $O_{1c}$-$C_{1c}$ | 1.392(7) | | |
| $O_{1c}$-$C_{3c}$ | 1.408(8) | Na-Cl | 2.896(2) |
| $O_{2c}$-$C_{2c}$ | 1.278(9) | | |
| $O_{2c}$-$C_{4c}$ | 1.409(8) | Na-$N_1$ | 3.098(4) |
| Na-$C_{11}$ | 2.967(5) | Na-$O_{1b}$ | 2.454(4) |
| Na-$C_{12}$ | 2.924(5) | Na-$O_{2b}$ | 2.483(4) |
| Na-$C_{13}$ | 3.015(5) | Na-$O_{1c}$ | 2.629(5) |
| Na-$C_{14}$ | 3.104(5) | Na-$O_{2c}$ | 2.408(5) |
| Na-$C_{g1}$[c] | 2.788(—) | | |

[a]The numbers in parentheses are the estimated standard deviations in the last significant digit.
[b]Atoms are labeled in agreement with FIG. 7.
[c]The symbol $C_{g1}$ is used to designate the center of gravity for the five-membered ring containing $N_1$, $C_{11}$, $C_{12}$, $C_{13}$, and $C_{14}$; this value is therefore listed without an estimated standard deviation.

TABLE XXII

Bond Angles Involving Nonhydrogen Atoms in Crystalline $[Cr(NC_4H_4)_3(Cl)(O_2C_2H_4(CH_3)_2)_3Na]^a$

| Type[b] | Angle, deg. | Type[b] | Angle, deg. |
|---|---|---|---|
| ClCr$N_1$ | 89.1(1) | ClCr$N_2$ | 173.9(1) |
| $N_1$Cr$N_2$ | 94.0(1) | ClCr$N_3$ | 94.5(1) |
| $N_1$Cr$N_3$ | 93.5(1) | $N_2$Cr$N_3$ | 90.5(1) |
| ClCr$O_{1a}$ | 86.9(1) | $N_1$Cr$O_{1a}$ | 171.9(1) |
| $N_2$Cr$O_{1a}$ | 89.4(1) | $N_3$Cr$O_{1a}$ | 93.8(1) |
| ClCr$O_{2a}$ | 88.9(1) | $N_1$Cr$O_{2a}$ | 94.7(1) |
| $N_2$Cr$O_{2a}$ | 85.7(1) | $N_3$Cr$O_{2a}$ | 171.2(1) |
| $O_{1a}$Cr$O_{2a}$ | 78.2(1) | | |
| Cr$N_1C_{11}$ | 124.4(3) | $C_{11}N_1C_{14}$ | 105.7(3) |
| Cr$N_1C_{14}$ | 128.6(3) | $C_{21}N_2C_{24}$ | 106.1(4) |
| Cr$N_2C_{21}$ | 126.6(3) | $C_{31}N_3C_{34}$ | 106.0(3) |
| Cr$N_2C_{24}$ | 126.5(3) | | |
| Cr$N_3C_{31}$ | 125.0(3) | Cr$O_{1a}C_{1a}$ | 113.5(2) |
| Cr$N_3C_{34}$ | 128.3(3) | Cr$O_{1a}C_{3a}$ | 122.5(3) |
| | | $C_{1a}O_{1a}C_{3a}$ | 110.5(3) |

TABLE XXII-continued

Bond Angles Involving Nonhydrogen Atoms in Crystalline $[Cr(NC_4H_4)_3(Cl)(O_2C_2H_4(CH_3)_2)_3Na]$ [a]

| Type [b] | Angle, deg. | Type [b] | Angle, deg. |
|---|---|---|---|
| $N_1C_{11}C_{12}$ | 110.3(4) | $CrO_{2a}C_{2a}$ | 107.4(2) |
| $C_{11}C_{12}C_{13}$ | 106.9(4) | $CrO_{2a}C_{4a}$ | 124.9(3) |
| $C_{12}C_{13}C_{14}$ | 106.5(4) | $C_{2a}O_{2a}C_{4a}$ | 111.8(3) |
| $N_1C_{14}C_{13}$ | 110.6(4) | $C_{1b}O_{1b}C_{3b}$ | 114.7(4) |
| $N_2C_{21}C_{22}$ | 109.7(4) | $C_{2b}O_{2b}C_{4b}$ | 115.6(5) |
| $C_{21}C_{22}C_{23}$ | 107.4(4) | $C_{1c}O_{1c}C_{3c}$ | 114.2(5) |
| $C_{22}C_{23}C_{24}$ | 107.1(4) | $C_{2c}O_{2c}C_{4c}$ | 116.0(5) |
| $N_2C_{24}C_{23}$ | 109.7(4) | | |
| $N_3C_{31}C_{32}$ | 110.3(4) | $O_{1a}C_{1a}C_{2a}$ | 105.8(3) |
| $C_{31}C_{32}C_{33}$ | 107.0(4) | $O_{2a}C_{2a}C_{1a}$ | 109.8(4) |
| $C_{32}C_{33}C_{34}$ | 106.6(4) | $O_{1b}C_{1b}C_{2b}$ | 112.8(5) |
| $N_3C_{34}C_{33}$ | 110.2(4) | $O_{2b}C_{2b}C_{1b}$ | 112.6(5) |
| | | $O_{1c}C_{1c}C_{2c}$ | 114.9(6) |
| ClNaC$_{g1}$ [c] | 83.6(—) | $O_{2c}C_{2c}C_{1c}$ | 121.1(6) |
| ClNaO$_{1b}$ | 89.5(1) | C$_{g1}$NaO$_{1b}$ [c] | 111.1(—) |
| ClNaO$_{2b}$ | 156.0(1) | C$_{g1}$NaO$_{2b}$ [c] | 110.2(—) |
| ClNaO$_{1c}$ | 108.2(1) | C$_{g1}$NaO$_{1c}$ [c] | 99.4(—) |
| ClNaO$_{2c}$ | 84.2(1) | C$_{g1}$NaO$_{2c}$ [c] | 155.9(—) |
| ClNaN$_1$ | 61.5(1) | $O_{1b}NaO_{2b}$ | 67.4(2) |
| ClNaC$_{11}$ | 73.3(2) | $O_{1b}NaO_{1c}$ | 146.4(2) |
| ClNaC$_{12}$ | 100.0(2) | $O_{1b}NaO_{2c}$ | 89.4(2) |
| ClNaC$_{13}$ | 104.4(2) | $O_{2b}NaO_{1c}$ | 89.3(2) |
| ClNaC$_{14}$ | 81.1(2) | $O_{2b}NaO_{2c}$ | 88.8(2) |
| | | $O_{1c}NaO_{2c}$ | 65.1(2) |
| N$_1$NaC$_{11}$ | 25.9(2) | | |
| N$_1$NaC$_{14}$ | 25.5(2) | N$_1$NaC$_{12}$ | 43.8(2) |
| C$_{11}$NaC$_{12}$ | 27.0(2) | N$_1$NaC$_{13}$ | 43.2(2) |
| C$_{12}$NaC$_{13}$ | 26.9(2) | C$_{11}$NaC$_{13}$ | 43.5(2) |
| C$_{13}$NaC$_{14}$ | 25.9(2) | C$_{12}$NaC$_{14}$ | 42.9(2) |
| | | C$_{11}$NaC$_{14}$ | 41.9(2) |

[a] The numbers in parentheses are the estimated standard deviations in the last significant digit.
[b] Atoms are labeled in agreement with FIG. 7.
[c] The symbol C$_{g1}$ is used to designate the center of gravity for the five-membered ring containing N$_1$, C$_{11}$, C$_{12}$, C$_{13}$, and C$_{14}$; this value is therefore listed without an estimated standard deviation.

While this invention has been described in detail for the purpose of illustration, it is not to be construed as limited thereby but is intended to cover all changes and modifications within the spirit and scope thereof.

That which is claimed is:

1. A polymerization process comprising contacting at least one mono-1-olefin with an alkyl aluminum activating compound and a catalyst prepared by a process comprising forming a mixture of and refluxing:
   (a) a chromium salt;
   (b) a metal amide, which is a pyrrolide; and
   (c) an electron pair donor solvent which can affect a reaction between the chromium salt and metal amide.

2. A process to polymerize olefins comprising contacting at least one mono-1-olefin with a composition comprising of $Cr_5(C_4H_4N)_{10}(C_4H_8O)_4$ supported on an inorganic oxide and an alkyl aluminum activating compound.

3. A process to polymerize olefins comprising contacting at least one mono-1-olefin with a composition comprising $Cr(C_4H_4N)_4Na_2 \cdot 2(OC_4H_8)$ supported on an inorganic oxide and an alkyl aluminum activating compound.

4. A process to polymerize olefins comprising contacting at least one mono-1-olefin with a composition comprising $Cr(C_4H_4N)_5(OC_4H_8)Na_2 \cdot 4(OC_4H_8)$ supported on an inorganic oxide and an alkyl aluminum activating compound.

5. A process to polymerize olefins comprising contacting at least one mono-1-olefin with a catalyst system prepared according to a process comprising:
   (a) forming a mixture of and refluxing a chromium salt, a metal amide which is a pyrrolide, and electron pair donor solvent which can affect a reaction between the chromium salt and metal amide;
   (b) recovering a chromium-containing compound from the mixture of (a);
   (c) reacting the chromium-containing compound of (b) with an aromatic compound and an alkyl aluminum activating compound to form a reaction product;
   (d) adding an inorganic oxide to the reaction product of (c); and
   (e) recovering a solid product.

6. A process to polymerize olefins comprising contacting at least one mono-1-olefin with a catalyst system prepared according to a process comprising:
   (a) forming a mixture of and refluxing a chromium salt, a metal amide which is a pyrrolide, and an electron pair donating solvent which can affect a reaction between the chromium salt and metal amide;
   (b) adding an inorganic oxide to the mixture of (a) to form a slurry;
   (c) recovering a supported chromium-containing solid product;
   (d) adding an alkyl aluminum activating compound to the solid product of (c); and
   (e) recovering a solid product.

7. A process to polymerize olefins comprising contacting at least one mono-1-olefin with a catalyst composition comprising $Cr(NC_4H_4)_3Cl(O_2C_2H_4(CH_3)_2)_3Na$ supported on an inorganic oxide and an alkyl aluminum activating compound.

8. A process to polymerize olefins comprising contacting at least one mono-1-olefin with a catalyst system prepared according to the process comprising:
   (a) forming a mixture of and refluxing a chromium salt, a metal amide which is a pyrrolide, and electron pair donor solvent which can affect a reaction between the chromium salt and metal amide;
   (b) recovering a chromium-containing compound from the mixture of (a); and
   (c) reacting the chromium-containing compound of (b) with an alkyl aluminum activating compound to form a reaction product.

9. A process according to claim 1 wherein said mono-1-olefin has from 2 to about 8 carbon atoms per molecule and said contacting occurs under slurry polymerization conditions.

10. A process according to claim 2 wherein said mono-1-olefin has from 2 to about 8 carbon atoms per molecule and said contacting occurs under slurry polymerization conditions.

11. A process according to claim 3 wherein said mono-1-olefin has from 2 to about 8 carbon atoms per molecule and said contacting occurs under slurry polymerization conditions.

12. A process according to claim 4 wherein said mono-1-olefin has from 2 to about 8 carbon atoms per molecule and said contacting occurs under slurry polymerization conditions.

13. A process according to claim 5 wherein said mono-1-olefin has from 2 to about 8 carbon atoms per molecule and said contacting occurs under slurry polymerization conditions.

14. A process according to claim 6 wherein said mono-1-olefin has from 2 to about 8 carbon atoms per molecule and said contacting occurs under slurry polymerization conditions.

15. A process according to claim 7 wherein said mono-1-olefin has from 2 to about 8 carbon atoms per molecule and said contacting occurs under slurry polymerization conditions.

16. A process according to claim 8 wherein said mono-1-olefin has from 2 to about 8 carbon atoms per molecule and said contacting occurs under slurry polymerization conditions.

17. A process according to claim 1 wherein said activating compound and said catalyst are supported on an inorganic oxide support.

18. A process according to claim 17 wherein said activating compound, said catalyst and said inorganic oxide support are combined in the presence of an aromatic hydrocarbon having from about 6 to about 50 carbon atoms per molecule.

19. A process according to claim 2 wherein said activating compound, $Cr_5(C_4H_4N)_{10}(C_4H_8O)_4$ and said inorganic oxide support are combined in the presence of an aromatic hydrocarbon having from about 6 to about 50 carbon atoms per molecule.

20. A process according to claim 3 wherein said activating compound, $Cr(C_4H_4N)_4Na_2.2(OC_4H_8)$ and said inorganic oxide support are combined in the presence of an aromatic hydrocarbon having from about 6 to about 50 carbon atoms per molecule.

21. A process according to claim 4 wherein said activating compound, $Cr(C_4H_0N)_5(OC_4H_8)Na_2.4(OC_4H_8)$ and said inorganic oxide support are combined in the presence of an aromatic hydrocarbon having from about 6 to about 50 carbon atoms per molecule.

22. A process according to claim 5 wherein said activating compound, said chromium-containing compound and said inorganic oxide support are combined in the presence of an aromatic hydrocarbon having from about 6 to about 50 carbon atoms per molecule.

23. A process according to claim 6 wherein said activating compound and said supported chromium-containing solid product are combined in the presence of an aromatic hydrocarbon having from about 6 to about 50 carbon atoms per molecule.

24. A process according to claim 7 wherein said activating compound, $Cr(NC_0H_4)_3Cl(O_2C_2H_4(CH_3)_2)_3Na$ and said inorganic oxide support are combined in the presence of an aromatic hydrocarbon having from about 6 to about 50 carbon atoms per molecule.

25. A process according to claim 8 wherein said activating compound, said chromium-containing compound and said inorganic oxide support are combined in the presence of an aromatic hydrocarbon having from about 6 to about 50 carbon atoms per molecule.

26. A process according to claim 1 wherein said activating compound is a trialkylaluminum compound.

27. A process according to claim 26 wherein said trialkyaluminum compound is triethylaluminum.

* * * * *

UNITED STATES PATENT AND TRADEMARK OFFICE
CERTIFICATE OF CORRECTION

PATENT NO. : 5,288,823

DATED : February 22, 1994

INVENTOR(S) : William K. Reagen

It is certified that error appears in the above-identified patent and that said Letters Patent is hereby corrected as shown below:

On the Title Page, item 75:

Front cover of original Letters Patent, Inventor's name "Reagan" should read ---Reagen---.

Front cover of original Letters Patent, Inventor's name "Brian K. Conroy" should be removed.

Signed and Sealed this

Twenty-third Day of August, 1994

Attest:

BRUCE LEHMAN

*Attesting Officer*     *Commissioner of Patents and Trademarks*